US 7,939,537 B2

(12) United States Patent
Summa et al.

(10) Patent No.: US 7,939,537 B2
(45) Date of Patent: May 10, 2011

(54) HIV INTEGRASE INHIBITORS

(75) Inventors: Vincenzo Summa, Rome (IT); Olaf Kinzel, Rome (IT); Monica Donghi, Rome (IT)

(73) Assignee: Istituto Di Ricerche Di Biologia Molecolare P. Angeletti S.p.A., Rome (IT)

( * ) Notice: Subject to any disclaimer, the term of this patent is extended or adjusted under 35 U.S.C. 154(b) by 14 days.

(21) Appl. No.: 11/992,531

(22) PCT Filed: Sep. 26, 2006

(86) PCT No.: PCT/EP2006/009410
§ 371 (c)(1),
(2), (4) Date: Mar. 25, 2008

(87) PCT Pub. No.: WO2007/039218
PCT Pub. Date: Apr. 12, 2007

(65) Prior Publication Data
US 2009/0221571 A1 Sep. 3, 2009

(51) Int. Cl.
A61K 31/519 (2006.01)
A61K 31/517 (2006.01)
A61K 31/535 (2006.01)
A61K 31/54 (2006.01)
A61K 31/497 (2006.01)
C07D 239/70 (2006.01)
C07D 295/00 (2006.01)
C07D 279/10 (2006.01)

(52) U.S. Cl. ............... 514/259.1; 514/258.1; 514/231.5; 514/226.8; 514/252.16; 544/282; 544/56; 544/98

(58) Field of Classification Search ............... 514/258.1, 514/259.1, 231.51; 544/282
See application file for complete search history.

(56) References Cited

U.S. PATENT DOCUMENTS

| 6,841,558 | B2 | 1/2005 | Anthony et al. |
| 6,919,351 | B2 | 7/2005 | Anthony et al. |
| 6,921,759 | B2 | 7/2005 | Anthony et al. |
| 7,091,209 | B2 | 8/2006 | Gardelli et al. |
| 7,109,186 | B2 | 9/2006 | Walker et al. |
| 7,169,780 | B2 | 1/2007 | Crescenzi et al. |
| 7,211,572 | B2 | 5/2007 | Miyazaki et al. |
| 7,217,713 | B2 | 5/2007 | Crescenzi et al. |
| 7,232,819 | B2 | 6/2007 | Di Francesco et al. |
| 7,279,487 | B2 | 10/2007 | Egbertson et al. |
| 2003/0055071 | A1 | 3/2003 | Anthony et al. |
| 2004/0229909 | A1 | 11/2004 | Kiyama et al. |
| 2005/0010048 | A1 | 1/2005 | Zhuang et al. |
| 2005/0130997 | A1 | 6/2005 | Avolio et al. |
| 2006/0046985 | A1 | 3/2006 | Crescenzi et al. |
| 2007/0083045 | A1 | 4/2007 | Di Francesco et al. |
| 2007/0123524 | A1 | 5/2007 | Crescenzi et al. |
| 2007/0161639 | A1 | 7/2007 | Jones et al. |
| 2007/0179196 | A1 | 8/2007 | Han et al. |

FOREIGN PATENT DOCUMENTS

| WO | WO 2004/058757 A1 | 7/2004 |
| WO | WO 2005/086700 A2 | 9/2005 |
| WO | WO 2005/118589 A1 | 12/2005 |
| WO | WO 2005/118593 A1 | 12/2005 |
| WO | WO 2006/116764 A1 | 11/2006 |

OTHER PUBLICATIONS

Goodman & Gilman's "The PHarmaceutical Basic of Therapeutics," 9th Edition, 1996, pp. 43-61.*
Pearl, L. et al. "A structural model for the retroviral proteases", Nature, 1987, vol. 329, pp. 351-354.
Power, M. et al. "Nucleotide Sequence of SRV-1, a Type D Simian Acquired Immune Deficiency Syndrome Retrovirus", Science, 1986, vol. 231, pp. 1567-1572.
Ratner, L. et al. "Complete nucleotide sequence of the AIDS virus, HTLV-III", Nature, 1985, vol. 313, pp. 277-284.
Tisler, M. et al. "An Improved Synthesis of Dimethyl Diacetoxyfumarate and Its Condensation with Heterocyclic Amines", OPPI Briefs, 1990, vol. 22, pp. 532-534.
Toh, H. et al. "Close structural resemblance between putative polymerase of a Drosophila transposable genetic element 17.6 and pol gene product of Moloney murine leukaemia virus", The EMBO Journal, 1985, vol. 4, pp. 1267-1272.

* cited by examiner

*Primary Examiner* — Shengjun Wang
(74) *Attorney, Agent, or Firm* — Kenneth R. Walton; Sheldon O. Heber

(57) ABSTRACT

Pyridopyrimidine carboxamide compounds of Formula I are inhibitors of HIV integrase and inhibitors of HIV replication:

(I)

[Chemical structure: pyridopyrimidine carboxamide with substituents $R^1$, $R^2$, $R^3$, $R^4$ on the pyridine ring, OH and carboxamide group $C(O)N(R^5)(R^6)$ on the pyrimidinone ring]

wherein $R^1$, $R^2$, $R^3$, $R^4$, $R^5$ and $R^6$ are defined herein. The compounds are useful for the prophylaxis or treatment of infection by HIV and the prophylaxis, treatment, or delay in the onset of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines.

13 Claims, No Drawings

HIV INTEGRASE INHIBITORS

CROSS-REFERENCE TO RELATED APPLICATIONS

This application is the National Stage of International Application No. PCT/EP2006/009410, filed on Sep. 26, 2006, which claims the benefit of U.S. Provisional Application No. 60/723,567 (filed Oct. 4, 2005), the disclosure of which is incorporated by reference herein in its entirety.

The present invention is directed to certain pyridopyrimidine carboxamide compounds and pharmaceutically acceptable salts thereof, their synthesis, and their use as inhibitors of the HIV integrase enzyme. The compounds and pharmaceutically acceptable salts thereof of the present invention are useful for preventing or treating infection by HIV and for preventing or treating or delaying the onset of AIDS.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

The following references are of interest as background:

Tisler et al., *Org. Prep. and Proc. Int.* 1990, 22: pp. 532-534, discloses the preparation of methyl 3-hydroxy-4-oxo-4H-pyrido[1,2-a]pyrimidine-2-carboxylate via the acid-catalyzed condensation of dimethyl diacetoxyfumarate with 2-aminopyridine. Methyl 3-hydroxy-7-methyl-4-oxo-4H-pyrido[1,2-a]pyrimidine-2-carboxylate is also disclosed.

U.S. Pat. No. 6,921,759 (corresponding to WO 02/30930), U.S. Pat. No. 6,919,351 (corresponding to WO 02/30426), and U.S. Pat. No. 6,841,558 (corresponding to WO 02/55079) each disclose certain 8-hydroxy-1,6-naphthyridine-7-carboxamides as HIV integrase inhibitors.

WO 02/036734 discloses certain aza- and polyaza-naphthalenyl ketones to be HIV integrase inhibitors.

WO 02/06246 discloses certain 2-aryldihydroxypyrimidine-4-carboxylic acids that are useful as hepatitis C viral polymerase inhibitors. WO 03/062211 discloses certain pyrimidinone derivatives that are viral polymerase inhibitors, especially the polymerase enzyme of the hepatitis C virus.

US 2004/0229909 discloses certain compounds having integrase inhibitory activity.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

WO 03/062204 discloses certain hydroxynaphthyridinone carboxamides that are useful as HIV integrase inhibitors.

WO 04/004657 discloses certain hydroxypyrrole derivatives that are HIV integrase inhibitors.

WO 20004/058576 discloses certain tetrahydro-4H-pyrido[1,2-a]pyrimidines and related compounds that are useful as HIV integrase inhibitors.

WO 2005/016927 discloses certain nitrogenous condensed ring compounds that are HIV integrase inhibitors.

SUMMARY OF THE INVENTION

The present invention is directed to certain 3-hydroxy-4-oxo-4H-pyrido[1,2-a]pyrimidine-2-carboxamide compounds. These compounds are useful in the inhibition of HIV integrase, the prevention of infection by HIV, the treatment of infection by HIV and in the prevention, treatment, and delay in the onset of AIDS and/or ARC, either as compounds or their pharmaceutically acceptable salts (when appropriate), or as pharmaceutical composition ingredients, whether or not in combination with other antiviral agents useful for treating HIV infection or AIDS, anti-infectives, immunomodulators, antibiotics or vaccines. More particularly, the present invention includes compounds of Formula I, and pharmaceutically acceptable salts thereof:

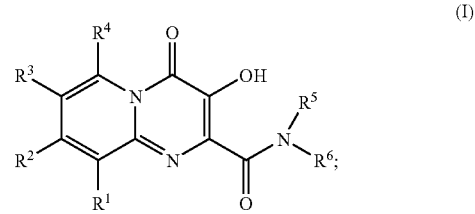

(I)

wherein
$R^1$, $R^2$, $R^3$, and $R^4$ are each independently:
(1) $R^A$,
(2) $R^E$,
(3) $C(O)R^A$,
(4) $C(O)R^E$,
(5) $C(O)OR^A$,
(6) $C(O)OR^E$,
(7) $C(O)N(R^A)R^B$,
(8) $C(O)N(R^A)R^E$,
(9) $OC(O)R^A$,
(10) $OC(O)R^E$,
(11) $OC(O)N(R^A)R^B$,

(12) $OC(O)N(R^A)R^E$,
(13) $N(R^A)R^B$,
(14) $N(R^A)R^E$,
(15) $N(R^A)C(O)R^B$,
(16) $N(R^A)C(O)R^E$,
(17) $N(R^A)C(O)OR^B$,
(18) $N(R^A)C(O)OR^E$,
(19) $N(R^A)C(O)N(R^A)R^B$,
(20) $N(R^A)C(O)N(R^A)R^E$,
(21) $N(R^A)C(O)C(O)N(R^A)R^B$,
(22) $N(R^A)C(O)C(O)N(R^A)R^E$,
(23) $N(R^A)S(O)_2R^B$,
(24) $N(R^A)S(O)_2R^E$,
(25) $N(R^A)S(O)_2N(R^A)R^B$,
(26) $N(R^A)S(O)_2N(R^A)R^E$,
(27) $OR^A$,
(28) $OR^E$,
(29) $SR^A$, $S(O)R^A$, or $S(O)_2R^A$,
(30) $SR^E$, $S(O)R^E$, or $S(O)_2R^E$,
(31) $S(O)_2N(R^A)R^B$,
(32) $S(O)_2N(R^A)R^E$,
(33) CycA, AryA, HetA, or HetR,
(34) $C_{1-6}$ alkyl substituted with CycA, AryA, HetA, or HetR,
(35) J-CycA, J-AryA, J-HetA, or J-HetR,
(36) $C_{1-6}$ alkylene-J-CycA, $C_{1-6}$ alkylene-J-AryA, $C_{1-6}$ alkylene-J-HetA, or $C_{1-6}$ alkylene-J-HetR,
(37) J-$C_{1-6}$ alkylene-CycA, J-$C_{1-6}$ alkylene-AryA, J-$C_{1-6}$ alkylene-HetA, or J-$C_{1-6}$ alkylene-HetR,
(38) $C_{1-6}$ alkylene-J-$C_{1-6}$ alkylene-CycA, $C_{1-6}$ alkylene-J-$C_{1-6}$ alkylene-AryA, $C_{1-6}$ alkylene-J-$C_{1-6}$ alkylene-HetA, or $C_{1-6}$ alkylene-J-$C_{1-6}$ alkylene-HetR, or
(39) halogen;
with the proviso that no more than one of $R^1$, $R^2$, $R^3$, and $R^4$ is other than $R^A$, $R^E$, or $C_{1-6}$ alkyl substituted with CycA, AryA, HetA, or HetR;
$R^5$ is $R^A$, $R^E$, or $R^F$;
$R^6$ is $C_{1-6}$ alkyl substituted with CycB, AryB, HetB, or HetS;
J is:
 (1) O,
 (2) S,
 (3) S(O),
 (4) $S(O)_2$,
 (5) C(O),
 (6) C(O)O,
 (7) $C(O)N(R^A)$,
 (8) $C(O)N(R^F)$,
 (9) $N(R^A)$,
 (10) $N(R^F)$,
 (11) $N(R^A)C(O)$,
 (12) $N(R^F)C(O)$,
 (13) $N(R^A)C(O)C(O)$,
 (14) $N(R^F)C(O)C(O)$,
 (15) $N(R^A)C(O)O$,
 (16) $N(R^F)C(O)O$
 (17) $N(R^A)S(O)_2$, or
 (18) $N(R^F)S(O)_2$;
each $R^A$ is independently H or $C_{1-6}$ alkyl;
each $R^B$ is independently H or $C_{1-6}$ alkyl;
each $R^E$ is independently $C_{1-6}$ haloalkyl or $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)$—O—$C_{1-6}$ alkyl, $N(R^A)C(O)R^B$, $N(R^A)CO_2R^B$, $N(R^A)S(O)_2R^B$, $N(R^A)S(O)_2N(R^A)R^B$, $OC(O)R^A$, $OC(O)N(R^A)R^B$, or $N(R^A)C(O)N(R^A)R^B$;
each $R^F$ is independently $C_{1-6}$ alkyl substituted with CycA, AryA, HetA, or HetR;

each CycA is independently $C_{3-8}$ cycloalkyl which is optionally substituted with a total of from 1 to 6 substituents, wherein:
 (i) from zero to 6 substituents are each independently:
  (1) halogen,
  (2) CN
  (3) $C_{1-6}$ alkyl,
  (4) OH,
  (5) O—$C_{1-6}$ alkyl,
  (6) $C_{1-6}$ haloalkyl, or
  (7) O—$C_{1-6}$ haloalkyl, and
 (ii) from zero to 2 substituents are each independently:
  (1) CycE,
  (2) AryE,
  (3) O-AryE,
  (4) HetE,
  (5) HetF, or
  (6) $C_{1-6}$ alkyl substituted with CycE, AryE, O-AryE, HetE, O-HetE, or HetF;
each AryA is independently aryl which is optionally substituted with a total of from 1 to 6 substituents, wherein:
 (i) from zero to 6 substituents are each independently:
  (1) $C_{1-6}$ alkyl,
  (2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)R^A$, $OC(O)N(R^A)R^B$, $N(R^A)C(O)N(R^A)R^B$, or $N(R^A)C(O)C(O)N(R^A)R^B$,
  (3) O—$C_{1-6}$ alkyl,
  (4) $C_{1-6}$ haloalkyl,
  (5) O—$C_{1-6}$ haloalkyl,
  (6) OH,
  (7) halogen,
  (8) CN,
  (9) $NO_2$,
  (10) $N(R^A)R^B$,
  (11) $C(O)N(R^A)R^B$,
  (12) $C(O)R^A$,
  (13) C(O)—$C_{1-6}$ haloalkyl,
  (14) $C(O)OR^A$,
  (15) $OC(O)R^A$,
  (16) $OC(O)N(R^A)R^B$,
  (17) $SR^A$,
  (18) $S(O)R^A$,
  (19) $S(O)_2R^A$,
  (20) $S(O)_2N(R^A)R^B$,
  (21) $N(R^A)S(O)_2R^B$,
  (22) $N(R^A)S(O)_2N(R^A)R^B$,
  (23) $N(R^A)C(O)R^B$,
  (24) $N(R^A)C(O)N(R^A)R^B$,
  (25) $N(R^A)C(O)$—$C(O)N(R^A)R^B$, or
  (26) $N(R^A)CO_2R^B$, and
 (ii) from zero to 2 substituents are each independently:
  (1) CycE,
  (2) O-CycE
  (3) AryE,
  (4) O-AryE,
  (5) HetE,
  (6) O-HetE,
  (7) HetF,
  (8) O-HetF or
  (9) $C_{1-6}$ alkyl substituted with CycE, O-CycE, AryE, O-AryE, HetE, O-HetE, O-HetF, or HetF;
each HetA is independently heteroaryl which is optionally substituted with a total of from 1 to 6 substituents, wherein:

(i) from zero to 6 substituents are each independently:
  (1) $C_{1-6}$ alkyl,
  (2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)R^A$, $OC(O)N(R^A)R^B$, $N(R^A)C(O)N(R^A)R^B$, or $N(R^A)C(O)C(O)N(R^A)R^B$,
  (3) O—$C_{1-6}$ alkyl,
  (4) $C_{1-6}$ haloalkyl,
  (5) O—$C_{1-6}$ haloalkyl,
  (6) OH,
  (7) oxo,
  (8) halogen,
  (9) CN,
  (10) $NO_2$,
  (11) $N(R^A)R^B$,
  (12) $C(O)N(R^A)R^B$,
  (13) $C(O)R^A$,
  (14) $C(O)$—$C_{1-6}$ haloalkyl,
  (15) $C(O)OR^A$,
  (16) $OC(O)R^A$,
  (17) $OC(O)N(R^A)R^B$,
  (18) $SR^A$,
  (19) $S(O)R^A$,
  (20) $S(O)_2R^A$,
  (21) $S(O)_2N(R^A)R^B$,
  (22) $N(R^A)S(O)_2R^B$,
  (23) $N(R^A)S(O)_2N(R^A)R^B$,
  (24) $N(R^A)C(O)R^B$,
  (25) $N(R^A)C(O)N(R^A)R^B$,
  (26) $N(R^A)C(O)$—$C(O)N(R^A)R^B$, or
  (27) $N(R^A)CO_2R^B$, and
(ii) from zero to 2 substituents are each independently:
  (1) CycE,
  (2) O-CycE
  (3) AryE,
  (4) O-AryE,
  (5) HetE,
  (6) O-HetE,
  (7) HetF,
  (8) O-HetF or
  (9) $C_{1-6}$ alkyl substituted with CycE, O-CycE, AryE, O-AryE, HetE, O-HetE, O-HetF, or HetF;
each HetR is independently (i) a 4- to 7-membered, saturated or mono-unsaturated heterocyclic ring containing at least one carbon atom and from 1 to 4 heteroatoms independently selected from N, O and S, where each S is optionally oxidized to S(O) or $S(O)_2$ or (ii) a 6- to 10-membered saturated or mono-unsaturated, bridged or fused heterobicyclic ring containing from 1 to 4 heteroatoms independently selected from N, O and S, where each S is optionally oxidized to S(O) or $S(O)_2$; and wherein the saturated or mono-unsaturated heterocyclic or heterobicyclic ring is optionally substituted with a total of from 1 to 4 substituents, wherein:
  (i) from zero to 4 substituents are each independently halogen, CN, $C_{1-6}$ alkyl, OH, oxo, $C(O)R^A$, $CO_2R^A$, $S(O)R^A$, $SR^A$, $S(O)_2R^A$, O—$C_{1-6}$ alkyl, $C_{1-6}$ haloalkyl, $C_{1-6}$ alkylene-CN, $C_{1-6}$ alkylene-OH, or $C_{1-6}$ alkylene-O—$C_{1-6}$ alkyl; and
  (ii) from zero to 2 substituents are each independently CycE, O-CycE, AryE, O-AryE, HetE, O-HetE, HetF, O-HetF, or $C_{1-6}$ alkyl substituted with CycE, O-CycE, AryE, O-AryE, HetE, O-HetE, HetF, O-HetF;
CycB independently has the same definition as CycA;
AryB independently has the same definition as AryA;
HetB independently has the same definition as HetA;
HetS independently has the same definition as HetR;
each aryl is independently (i) phenyl, (ii) a 9- or 10-membered bicyclic, fused carbocylic ring system in which at least one ring is aromatic, or (iii) an 11- to 14-membered tricyclic, fused carbocyclic ring system in which at least one ring is aromatic;
each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or $S(O)_2$;
each CycE is independently $C_{3-8}$ cycloalkyl which is optionally substituted with a total of from 1 to 4 substituents, wherein:
  (i) from zero to 4 substituents are each independently halogen, $C_{1-6}$ alkyl, OH, O—$C_{1-6}$ alkyl, $C_{1-6}$ haloalkyl, or O—$C_{1-6}$ haloalkyl, and
  (ii) from zero to 2 substituents are each independently CycG, AryG, HetG, HetH, or $C_{1-6}$ alkyl substituted with CycG, AryG, O-AryG, HetG, or HetH;
each AryE is independently phenyl or naphthyl, wherein the phenyl or naphthyl is optionally substituted with a total of from 1 to 5 substituents, wherein:
  (i) from zero to 5 substituents are each independently halogen, CN, $NO_2$, $C_{1-6}$ alkyl, $C_{1-6}$ haloalkyl, OH, O—$C_{1-6}$ alkyl, O—$C_{1-6}$ haloalkyl, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$, and
  (ii) from zero to 2 substituents are each independently CycG, AryG, HetG, HetH, or $C_{1-6}$ alkyl substituted with CycG, AryG, O-AryG, HetG, or HetH;
each HetE is independently (i) a 5- or 6-membered heteroaromatic ring containing from 1 to 4 heteroatoms independently selected from N, O and S, wherein each N is optionally in the form of an oxide, or (ii) a 9- or 10-membered fused heterobicyclic ring selected from 2,3-dihydrobenzo-1,4-dioxinyl and benzo-1,3-dioxolyl; and wherein the heteroaromatic ring or the heterobicyclic ring is optionally substituted with a total of from 1 to 4 substituents wherein:
  (i) from zero to 4 substituents are each independently halogen, $C_{1-6}$ alkyl, $C_{1-6}$ haloalkyl, O—$C_{1-6}$ alkyl, O—$C_{1-6}$ haloalkyl, OH, $C(O)R^A$, $CO_2R^A$, $SO_2R^A$, $N(R^A)R^B$, $N(R^A)C(O)N(R^A)R^B$, or $N(R^A)CO_2R^B$, and
  (ii) from zero to 2 substituents are each independently CycG, AryG, HetG, HetH, or $C_{1-6}$ alkyl substituted with CycG, AryG, O-AryG, HetG, or HetH;
each HetF is independently a 4- to 7-membered, saturated or mono-unsaturated heterocyclic ring containing at least one carbon atom and from 1 to 4 heteroatoms independently selected from N, O and S, where each S is optionally oxidized to S(O) or $S(O)_2$, and wherein the saturated or mono-unsaturated heterocyclic ring is optionally substituted with a total of from 1 to 4 substituents, wherein:
  (i) from zero to 4 substituents are each independently halogen, CN, $C_{1-6}$ alkyl, OH, oxo, O—$C_{1-6}$ alkyl, $C_{1-6}$ haloalkyl, O—$C_{1-6}$ haloalkyl, $C(O)R^A$, $CO_2R^A$, or $SO_2R^A$, and
  (ii) from zero to 2 substituents are each independently CycG, AryG, HetG, HetH, or $C_{1-6}$ alkyl substituted with CycG, AryG, O-AryG, HetG, or HetH;

each CycG is independently $C_{3-8}$ cycloalkyl which is optionally substituted with from 1 to 4 substituents, each of which is independently halogen, $C_{1-6}$ alkyl, OH, O—$C_{1-6}$ alkyl, $C_{1-6}$ haloalkyl, or O—$C_{1-6}$ haloalkyl;

each AryG is independently phenyl or naphthyl, wherein the phenyl or naphthyl is optionally substituted with from 1 to 5 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$;

each HetG is independently a 5- or 6-membered heteroaromatic ring containing from 1 to 4 heteroatoms independently selected from N, O and S, wherein each N is optionally in the form of an oxide, and wherein the heteroaromatic ring is optionally substituted with from 1 to 4 substituents each of which is independently halogen, $C_{1-6}$ alkyl, $C_{1-6}$ haloalkyl, O—$C_{1-6}$ alkyl, O—$C_{1-6}$ haloalkyl, OH, $C(O)R^A$, $CO_2R^A$, $SO_2R^A$, $N(R^A)R^B$, $N(R^A)C(O)N(R^A)R^B$, or $N(R^A)CO_2R^B$; and each HetH is independently a 4- to 7-membered, saturated or mono-unsaturated heterocyclic ring containing at least one carbon atom and from 1 to 4 heteroatoms independently selected from N, O and S, where each S is optionally oxidized to S(O) or $S(O)_2$, and wherein the saturated or mono-unsaturated heterocyclic ring is optionally substituted with from 1 to 4 substituents, each of which is independently halogen, CN, $C_{1-6}$ alkyl, OH, oxo, O—$C_{1-6}$ alkyl, $C_{1-6}$ haloalkyl, O—$C_{1-6}$ haloalkyl, $C(O)R^A$, $CO_2R^A$, or $SO_2R^A$.

The present invention also includes pharmaceutical compositions containing a compound of Formula I or a pharmaceutically acceptable salt thereof. The present invention further includes methods for the treatment of AIDS, the delay in the onset of AIDS, the prophylaxis of AIDS, the prophylaxis of infection by HIV, and the treatment of infection by HIV.

Other embodiments, aspects and features of the present invention are either further described in or will be apparent from the ensuing description, examples and appended claims.

DETAILED DESCRIPTION OF THE INVENTION

The present invention includes compounds of Formula I above, and pharmaceutically acceptable salts thereof. These compounds and their pharmaceutically acceptable salts are HIV integrase inhibitors (e.g., HIV-1 integrase inhibitors).

Embodiments of the present invention include those in which the compound of Formula I is as originally defined above (i.e., as defined in the Summary of the Invention), except that one or more of the original definitions of the variables is(are) replaced by variable definition(s) (i) to (xi) as follows:

(i-a) $R^1$ is as originally defined above and $R^2$, $R^3$, and $R^4$ are each $R^A$; or $R^3$ is as originally defined above and $R^1$, $R^2$, and $R^4$ are each $R^A$;

(i-b) $R^1$ is as originally defined above and $R^2$, $R^3$, and $R^4$ are each $R^A$;

(i-c) $R^3$ is as originally defined above and $R^1$, $R^2$, and $R^4$ are each $R^A$;

(i-d) $R^1$ is as originally defined above and $R^2$, $R^3$, and $R^4$ are each H; or $R^3$ is as originally defined above and $R^1$, $R^2$, and $R^4$ are each H;

(i-e) $R^1$ is as originally defined above and $R^2$, $R^3$, and $R^4$ are each H;

(i-f) $R^3$ is as originally defined above and $R^1$, $R^2$, and $R^4$ are each H;

(i-g) one of $R^1$, $R^2$, $R^3$, and $R^4$ is:
  (1) H,
  (2) $C_{1-6}$ alkyl,
  (3) $C_{1-6}$ alkyl substituted with $N(R^A)R^B$ or $N(R^A)O$—$C_{1-6}$ alkyl,
  (4) $N(R^A)R^B$,
  (5) $N(R^A)C(O)$—$C_{1-6}$ alkyl, wherein the alkyl is optionally substituted with $N(R^A)R^B$ or $S(O)_2R^A$,
  (6) $N(R^A)C(O)C(O)N(R^A)R^B$,
  (7) AryA,
  (8) HetR,
  (9) $C_{1-6}$ alkyl substituted with HetR,
  (10) $N(R^A)C(O)C(O)$-HetR,
  (11) $N(R^A)C(O)$-AryA,
  (12) $N(R^A)C(O)$-HetA,
  (13) $N(R^A)C(O)$-HetR,
  (14) $N(R^A)C(O)$—$C_{1-6}$ alkylene-AryA,
  (15) $N(R^A)C(O)$—$C_{1-6}$ alkylene-HetA,
  (16) $N(R^A)C(O)$—$C_{1-6}$ alkylene-HetR,
  (17) $C_{1-6}$ alkylene-$N(R^A)C(O)$-AryA,
  (18) $C_{1-6}$ alkylene-$N(R^A)C(O)$-HetA,
  (19) $N(R^A)C(O)O$—$C_{1-6}$ alkylene-AryA,
  (20) $N(R^A)C(O)O$—$C_{1-6}$ alkylene-HetA,
  (21) O—$C_{1-6}$ alkylene-AryA,
  (22) O—$C_{1-6}$ alkylene-HetA, or
  (23) halogen; and the other three of $R^1$, $R^2$, $R^3$, and $R^4$ are each independently H or $C_{1-6}$ alkyl;

(i-h) $R^1$, $R^2$, $R^3$, and $R^4$ are as defined in (i-g) above, except that the definition of $R^1$ is selected from one of groups (1) to (6) and (8) to (22) (i.e., in this embodiment, $R^1$ excludes (7) AryA and (23) halogen); or (i-i) $R^1$ is:
  (1) H,
  (2) $C_{1-4}$ alkyl,
  (3) $C_{1-4}$ alkyl substituted with $N(R^A)R^B$ or $N(R^A)O$—$C_{1-4}$ alkyl,
  (4) $N(R^A)R^B$,
  (5) $N(R^A)C(O)$—$C_{1-4}$ alkyl,
  (6) $N(R^A)C(O)$—$(CH_2)_{1-2}N(R^A)R^B$,
  (7) $N(R^A)C(O)$—$(CH_2)_{1-2}S(O)_2R^A$,
  (8) $N(R^A)C(O)C(O)N(R^A)R^B$,
  (9) HetR,
  (10) $(CH_2)_{1-2}$-HetR,
  (11) $N(R^A)C(O)C(O)$-HetR,
  (12) $N(R^A)C(O)$-AryA,
  (13) $N(R^A)C(O)$-HetA,
  (14) $N(R^A)C(O)$-HetR,
  (15) $N(R^A)C(O)$—$(CH_2)_{1-2}$-AryA,
  (16) $N(R^A)C(O)$—$(CH_2)_{1-2}$-HetA,
  (17) $N(R^A)C(O)$—$(CH_2)_{1-2}$-HetR,
  (18) $(CH_2)_{1-2}$—$N(R^A)C(O)$-AryA,
  (19) $(CH_2)_{1-2}$—$N(R^A)C(O)$-HetA,
  (20) $N(R^A)C(O)O$—$(CH_2)_{1-2}$-AryA,
  (21) $N(R^A)C(O)O$—$(CH_2)_{1-2}$-HetA,
  (22) O—$(CH_2)_{1-2}$-AryA, or
  (23) O—$(CH_2)_{1-2}$-HetA; and $R^2$, $R^3$, and $R^4$ are each independently H or $C_{1-4}$ alkyl;

(ii-a) $R^5$ is $R^A$;

(ii-b) $R^5$ is H or $C_{1-4}$ alkyl; or (ii-c) $R^5$ is H;

(iii-a) $R^6$ is $CH_2$-AryB;

(iii-b) $R^6$ is:

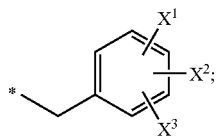

the asterisk * denotes the point of attachment of $R^6$ to the rest of the compound; $X^1$ and $X^2$ are each independently:
(1) H,
(2) $C_{1-6}$ alkyl,
(3) OH
(4) O—$C_{1-6}$ alkyl,
(5) $C_{1-6}$ haloalkyl,
(6) O—$C_{1-6}$ haloalkyl,
(7) halogen,
(8) CN,
(9) $N(R^A)R^B$,
(10) $C(O)N(R^A)R^B$,
(11) $SR^A$,
(12) $S(O)R^A$,
(13) $SO_2R^A$,
(14) $N(R^A)SO_2R^B$,
(15) $N(R^A)SO_2N(R^A)R^B$,
(16) $N(R^A)C(O)R^B$,
(17) $N(R^A)C(O)C(O)N(R^A)R^B$, or
(18) HetE;
or alternatively $X^1$ and $X^2$ are respectively located on adjacent carbons in the phenyl ring and together form methylenedioxy or ethylenedioxy; and
$X^3$ is:
(1) H,
(2) $C_{1-6}$ alkyl,
(3) O—$C_{1-6}$ alkyl,
(4) $C_{1-6}$ haloalkyl,
(5) O—$C_{1-6}$ haloalkyl, or
(6) halogen;
(iii-c) $R^6$ is as defined in (ii-c), except that: $X^1$ and $X^2$ in the definition of $R^6$ are each independently: (1) H, (2) $C_{1-4}$ alkyl, (3) $C_{1-4}$ haloalkyl, (4) OH, (5) O—$C_{1-4}$ alkyl, (6) halogen, (7) CN, (8) C(=O)NH$_2$, (9) C(=O)NH(—$C_{1-4}$ alkyl), (10) C(=O)N(—$C_{1-4}$ alkyl)$_2$, or (11) SO$_2$—$C_{1-4}$ alkyl; or alternatively $X^1$ and $X^2$ are respectively located on adjacent carbons in the phenyl ring and together form methylenedioxy or ethylenedioxy; and $X^3$ is H, halogen, $C_{1-4}$ alkyl, or O—$C_{1-4}$ alkyl;
(iii-d) $R^6$ is:

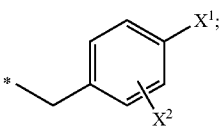

wherein the asterisk * denotes the point of attachment of $R^1$ to the rest of the compound; $X^1$ is H, bromo, chloro, fluoro, or methoxy; and $X^2$ is H, bromo, chloro, fluoro, methoxy, $C_{1-4}$ alkyl, CF$_3$, OCF$_3$, CN, or SO$_2$($C_{1-4}$ alkyl);
(iii-e) $R^6$ is CH$_2$-AryB; and AryB is 4-fluorophenyl or 3-chloro-4-fluorophenyl;
(iii-f) $R^6$ is CH$_2$-AryB; and AryB is 4-fluorophenyl; or
(iii-g) $R^6$ is CH$_2$-AryB; and AryB is 3-chloro-4-fluorophenyl;

(iv-a) AryA is phenyl or naphthyl, wherein the phenyl or naphthyl is optionally substituted with a total of from 1 to 5 substituents, wherein:
(i) from zero to 5 substituents are each independently:
(1) $C_{1-4}$ alkyl,
(2) O—$C_{1-4}$ alkyl,
(3) $C_{1-4}$ haloalkyl,
(4) O—$C_{1-4}$ haloalkyl,
(5) OH,
(6) halogen,
(7) CN,
(8) NO$_2$,
(9) $N(R^A)R^B$,
(10) $C(O)N(R^A)R^B$,
(11) C(O)—$C_{1-4}$ alkyl,
(12) CO$_2$—$C_{1-4}$ alkyl,
(13) S—$C_{1-4}$ alkyl,
(14) S(O)—$C_{1-4}$ alkyl,
(15) SO$_2$—$C_{1-4}$ alkyl,
(16) $SO_2N(R^A)R^B$,
(17) $SO_2N(R^A)C(O)$—$C_{1-4}$ alkyl, or
(18) $N(R^A)C(O)$—$C_{1-4}$ alkyl, and
(ii) from zero to 1 substituent is AryE, HetE, CH$_2$-AryE, or CH$_2$-HetE; or
(iv-b) AryA is phenyl which is optionally substituted with a total of from 1 to 3 substituents, wherein:
(i) from zero to 3 substituents are each independently bromo chloro, fluoro, methoxy, $C_{1-4}$ alkyl, CF$_3$, OCF$_3$, CN, SO$_2$($C_{1-4}$ alkyl), or N($C_{1-4}$ alkyl)$_2$, and
(ii) from zero to 1 substituent is:

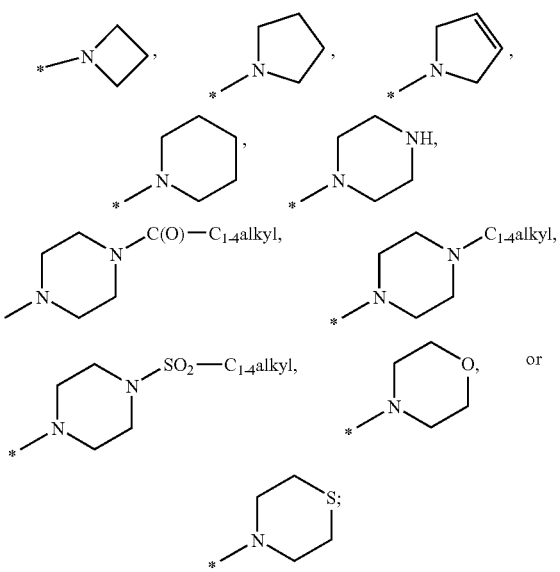

wherein the asterisk denotes the point of attachment of the heterocyclic ring to the rest of the molecule;
(v-a) HetA is (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing a total of from 1 to 4 heteroatoms independently selected from zero to 4 N atoms, zero to 2 O atoms, and zero to 2 S atoms, wherein either one or both of the rings contain one or more of the heteroatoms, at least one ring is aromatic, each N is optionally in the form of an oxide, and each S in a ring which is not aromatic is optionally S(O) or S(O)$_2$; wherein the heteroaromatic ring or the bicyclic, fused ring system is optionally substituted with a total of from 1 to 4 substituents, wherein:

(i) from zero to 4 substituents are each independently:
  (1) $C_{1-4}$ alkyl,
  (2) O—$C_{1-4}$ alkyl,
  (3) $C_{1-4}$ haloalkyl,
  (4) O—$C_{1-4}$ haloalkyl,
  (5) OH,
  (6) Cl, Br, or F,
  (7) CN,
  (8) C(O)N(R$^A$)R$^B$,
  (9) S(O)$_2$—$C_{1-4}$ alkyl, or
  (10) S(O)$_2$N(R$^A$)R$^B$, and
(ii) from zero to 1 substituent is AryE, HetE, CH$_2$-AryE, or CH$_2$-HetE; or (v-b) HetA is a heteroaromatic ring selected from the group consisting of pyrrolyl, pyrazolyl, imidazolyl, pyridinyl, pyrimidinyl, pyrazinyl, oxazolyl, isoxazolyl, thiazolyl, isothiazolyl, and oxadiazolyl, wherein the heteroaromatic ring is optionally substituted with from 1 to 2 substituents each of which is independently a $C_{1-4}$ alkyl;

(vi-a) HetR is a 4- to 7-membered, saturated or mono-unsaturated heterocyclic ring or a 6- to 10-membered saturated or mono-unsaturated, bridged or fused heterobicyclic ring, wherein the heterocyclic or heterobicyclic ring contains a nitrogen atom which is directly attached to the rest of the molecule and optionally contains an additional heteroatom selected from N, O, and S, where the S is optionally oxidized to S(O) or S(O)$_2$; and wherein the heterocyclic or heterobicyclic ring is optionally substituted with a total of from 1 to 4 substituents, wherein:

(i) from zero to 4 substituents are each independently Cl, Br, F, $C_{1-4}$ alkyl, OH, oxo, C(O)—$C_{1-4}$ alkyl, S(O)$_2$—$C_{1-4}$ alkyl, O—$C_{1-4}$ alkyl, O—$C_{1-4}$ haloalkyl, or $C_{1-4}$ haloalkyl; and
(ii) from zero to 1 substituent is AryE, HetE, CH$_2$-AryE, or CH$_2$-HetE;

(vi-b) HetR is a heterocyclic or heterobicyclic ring selected from the group consisting of:

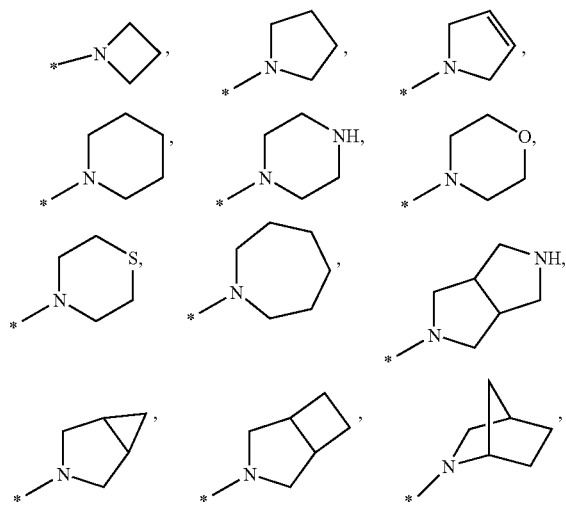

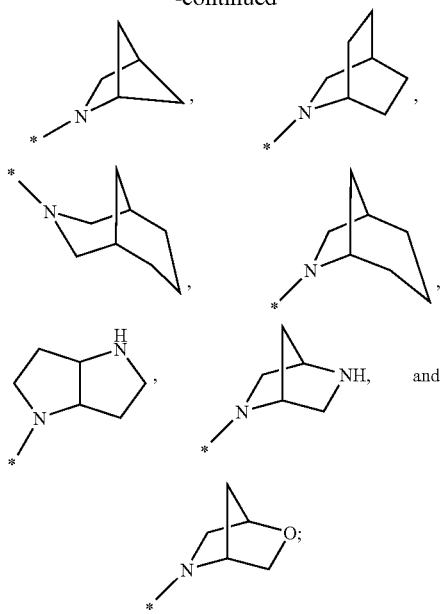

wherein the asterisk denotes the point of attachment of the heterocyclic or heterobicyclic ring to the rest of the molecule, and wherein the heterocyclic or heterobicyclic ring is optionally substituted with a total of from 1 to 4 substituents, each of which is independently $C_{1-4}$ alkyl, C(O)—$C_{1-4}$ alkyl, S(O)$_2$—$C_{1-4}$ alkyl, O—$C_{1-4}$ alkyl, $C_{1-4}$ fluoroalkyl, O—$C_{1-4}$ fluoroalkyl, oxo, Cl, Br, or F; or (vi-c) HetR is a heterocyclic ring selected from the group consisting of:

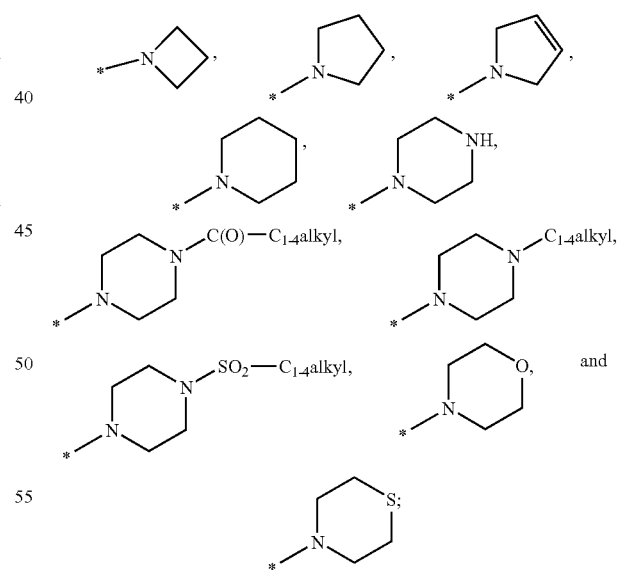

wherein the asterisk denotes the point of attachment of the heterocyclic ring to the rest of the molecule;

(vii) AryB is phenyl which is optionally substituted with from 1 to 5 substituents wherein:
(i) from zero to 5 substituents are each independently:
  (1) $C_{1-4}$ alkyl,
  (2) OH
  (3) O—$C_{1-4}$ alkyl, (4) $C_{1-4}$ haloalkyl,
(5) O—$C_{1-4}$ haloalkyl,
(6) halogen,
(7) CN,
(8) $N(R^A)R^B$,
(9) $C(O)N(R^A)R^B$,
(10) $SR^A$,
(11) $S(O)R^A$,
(12) $SO_2R^A$,
(13) $N(R^A)SO_2R^B$,
(14) $N(R^A)SO_2N(R^A)R^B$,
(15) $N(R^A)C(O)R^B$, or
(16) $N(R^A)C(O)C(O)N(R^A)R^B$, and
(ii) from zero to 1 substituent is AryE, HetE, $CH_2$-AryE, or $CH_2$-HetE;
(viii) AryE is phenyl which is optionally substituted with from 1 to 3 substituents each of which is independently $C_{1-4}$ alkyl, O—$C_{1-4}$ alkyl, $C_{1-4}$ fluoroalkyl, O—$C_{1-4}$ fluoroalkyl, Cl, Br, F, CN, $C(O)N(R^A)R^B$, $S(O)_2$—$C_{1-4}$ alkyl, or $S(O)_2N(R^A)R^B$;
(ix) HetE is a 5- or 6-membered heteroaromatic ring containing from 1 to 4 heteroatoms independently selected from N, O and S, wherein each N is optionally in the form of an oxide, wherein the heteroaromatic ring is optionally substituted with from 1 to 3 substituents each of which is independently Cl, Br, F, CN, $NO_2$, $C_{1-4}$ alkyl, $C_{1-4}$ fluoroalkyl, OH, O—$C_{1-4}$ alkyl, or O—$C_{1-4}$ fluoroalkyl;
(x-a) each $R^A$ is independently H or $C_{1-4}$ alkyl;
(x-b) each $R^A$ is independently H or $C_{1-3}$ alkyl;
(x-c) each $R^A$ is independently H, methyl or ethyl; or
(x-d) each $R^A$ is independently H or methyl;
(xi-a) each $R^B$ is independently H or $C_{1-4}$ alkyl;
(xi-b) each $R^B$ is independently H or $C_{1-3}$ alkyl;
(xi-c) each $R^B$ is independently H, methyl or ethyl; or
(xi-d) each $R^B$ is independently H or methyl.

Compound embodiments of particular interest herein are referred to as compound classes.

A first class of the present invention includes compounds of Formula I, and pharmaceutically acceptable salts thereof, wherein $R^1$, $R^2$, $R^3$, and $R^4$ are as defined in item (i-h) above; $R^5$ is H or $C_{1-6}$ alkyl; $R^6$ is $CH_2$-AryB; and all other variables are as originally defined above.

A second class of the present invention includes compounds of Formula I, and pharmaceutically acceptable salts thereof, wherein $R^1$, $R^2$, $R^3$, and $R^4$ are as defined in item (i-i) above; $R^5$ is H or $C_{1-4}$ alkyl; $R^6$ is $CH_2$-AryB; each $R^A$ is independently H or $C_{1-4}$ alkyl; each $R^B$ is independently H or $C_{1-4}$ alkyl; AryA is as defined in item (iv-a); HetA is as defined in item (v-a); HetR is as defined in item (vi-a); AryB is as defined in item (vii); AryE is as defined in item (viii); and HetE is as defined in item (ix).

A third class of the present invention includes compounds of Formula II, and pharmaceutically acceptable salts thereof:

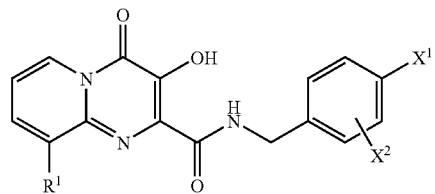

(II)

wherein:
$R^1$ is:
(1) H,
(2) $C_{1-4}$ alkyl,
(3) $CH_2N(C_{1-4}$ alkyl$)_2$,
(4) $CH_2N(C_{1-4}$ alkyl)—O—$C_{1-4}$ alkyl,
(5) $N(C_{1-4}$ alkyl$)_2$,
(6) $N(C_{1-4}$ alkyl)C(O)—$C_{1-4}$ alkyl,
(7) $N(C_{1-4}$ alkyl)C(O)$CH_2N(C_{1-4}$ alkyl$)_2$,
(8) $N(C_{1-4}$ alkyl)C(O)$CH_2S(O)_2$—$C_{1-4}$ alkyl,
(9) $N(C_{1-4}$ alkyl)C(O)C(O)($C_{1-4}$ alkyl$)_2$,
(10) HetR,
(11) $CH_2$-HetR,
(12) $N(C_{1-4}$ alkyl)C(O)C(O)-HetR,
(13) N(H)C(O)-AryA,
(14) $N(C_{1-4}$ alkyl)C(O)-AryA,
(15) N(H)C(O)-HetA,
(16) $N(C_{1-4}$ alkyl)C(O)-HetA,
(17) N(H)C(O)-HetR,
(18) $N(C_{1-4}$ alkyl)C(O)-HetR,
(19) N(H)C(O)—$(CH_2)_{1-2}$-AryA,
(20) $N(C_{1-4}$ alkyl)C(O)—$(CH_2)_{1-2}$-AryA,
(21) N(H)C(O)—$(CH_2)_{1-2}$-HetA,
(22) $N(C_{1-4}$ alkyl)C(O)—$(CH_2)_{1-2}$-HetA,
(23) $N(C_{1-4}$ alkyl)C(O)$CH_2$-HetR,
(24) $CH_2N(H)C(O)$-AryA,
(25) $CH_2N(C_{1-4}$ alkyl)C(O)-AryA,
(26) $CH_2N(H)C(O)$-HetA,
(27) $CH_2N(C_{1-4}$ alkyl)C(O)-HetA,
(28) N(H)C(O)O$CH_2$-AryA,
(29) $N(C_{1-4}$ alkyl)C(O)O$CH_2$-AryA,
(30) N(H)C(O)O$CH_2$-HetA,
(31) $N(C_{1-4}$ alkyl)C(O)O$CH_2$-HetA,
(32) O$CH_2$-AryA, or
(33) O$CH_2$-HetA;

AryA is phenyl which is optionally substituted with from 1 to 3 substituents each of which is independently bromo chloro, fluoro, methoxy, $C_{1-4}$ alkyl, $CF_3$, $OCF_3$, CN, or $SO_2(C_{1-4}$ alkyl);

HetA is a heteroaromatic ring selected from the group consisting of pyrrolyl, pyrazolyl, imidazolyl, pyridinyl, pyrimidinyl, pyrazinyl, oxazolyl, isoxazolyl, thiazolyl, isothiazolyl, and oxadiazolyl, wherein the heteroaromatic ring is optionally substituted with from 1 to 2 substituents each of which is independently a $C_{1-4}$ alkyl; and HetR is a heterocyclic ring selected from the group consisting of:

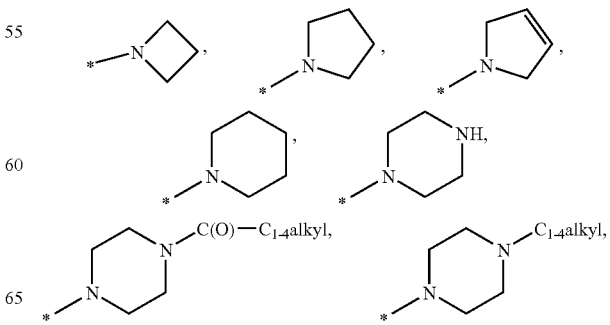

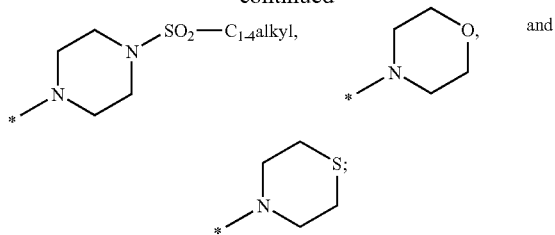

wherein the asterisk denotes the point of attachment of the heterocyclic ring to the rest of the molecule;

$X^1$ is H, bromo, chloro, fluoro, or methoxy; and $X^2$ is H, bromo, chloro, fluoro, methoxy, $C_{1-4}$ alkyl, $CF_3$, $OCF_3$, CN, or $SO_2(C_{1-4}$ alkyl).

A fourth class of the present invention includes compounds of Formula I, and pharmaceutically acceptable salts thereof, wherein $R^3$ is (1) halogen, (2) AryA, or (3) HetA; $R^1$, $R^2$, and $R^4$ are each independently H or $C_{1-6}$ alkyl; $R^5$ is H or $C_{1-6}$ alkyl; $R^6$ is $CH_2$-AryB; and all other variables are as originally defined above.

A sub-class of the fourth class includes compounds of Formula III, and pharmaceutically acceptable salts thereof:

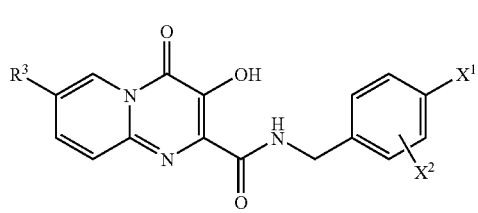

(III)

wherein:

$R^3$ is:
   (1) bromine,
   (2) AryA, or
   (3) HetA;

AryA is phenyl which is optionally substituted with a total of from 1 to 3 substituents, wherein:
   (i) from zero to 3 substituents are each independently bromo chloro, fluoro, methoxy, $C_{1-4}$ alkyl, $CF_3$, $OCF_3$, CN, $SO_2(C_{1-4}$ alkyl), or $N(C_{1-4}$ alkyl)$_2$, and
   (ii) from zero to 1 substituent is:

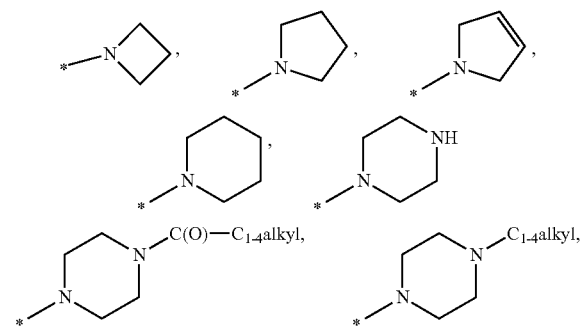

wherein the asterisk denotes the point of attachment of the heterocyclic ring to the rest of the molecule;

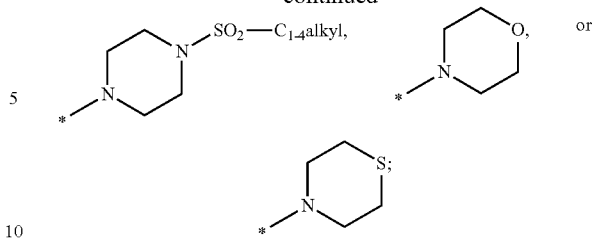

HetA is a heteroaromatic ring selected from the group consisting of pyrrolyl, pyrazolyl, imidazolyl, pyridinyl, pyrimidinyl, pyrazinyl, oxazolyl, isoxazolyl, thiazolyl, isothiazolyl, and oxadiazolyl, wherein the heteroaromatic ring is optionally substituted with from 1 to 2 substituents each of which is independently a $C_{1-4}$ alkyl;

$X^1$ is H, bromo, chloro, fluoro, or methoxy; and $X^2$ is H, bromo, chloro, fluoro, methoxy, $C_{1-4}$ alkyl, $CF_3$, $OCF_3$, CN, or $SO_2(C_{1-4}$ alkyl).

Another embodiment of the present invention is a compound, or a pharmaceutically acceptable salt thereof, selected from the group consisting of the compounds set forth in Examples 1 to 35. Another embodiment of the present invention is a compound, or a pharmaceutically acceptable salt thereof, selected from the group consisting of the compounds set forth in Examples 1 to 4 and 6 to 33. Another embodiment of the present invention is a compound, or a pharmaceutically acceptable salt thereof, selected from the group consisting of the compounds set forth in Examples 5 and 35.

Another embodiment of the present invention is a compound of Formula I, or a pharmaceutically acceptable salt thereof, as originally defined or as defined in any of the foregoing embodiments, classes, or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. A compound or salt of 100% purity is one which is free of detectable impurities as determined by one or more standard methods of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

Other embodiments of the present invention include the following:

(a) A pharmaceutical composition comprising an effective amount of a compound of Formula I and a pharmaceutically acceptable carrier.

(b) A pharmaceutical composition which comprises the product prepared by combining (e.g., mixing) an effective amount of a compound of Formula I and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, non-nucleoside HIV reverse transcriptase inhibitors, nucleoside HIV reverse transcriptase inhibitors, and HIV fusion inhibitors.

(e) A pharmaceutical combination which is (i) a compound of Formula I and (ii) an anti-HIV agent selected from the group consisting of HIV antiviral agents, immunomodulators, and anti-infective agents; wherein the compound of Formula I and the anti-HIV agent are each employed in an amount that renders the combination effective for the inhibition of HIV integrase, for the treatment or prophylaxis of infection by HIV, or for the treatment, prophylaxis or delay in the onset of AIDS.

(f) The combination of (e), wherein the anti-HIV agent is an antiviral selected from the group consisting of HIV protease inhibitors, non-nucleoside HIV reverse transcriptase inhibitors, nucleoside HIV reverse transcriptase inhibitors, and HIV fusion inhibitors.

(g) A method of inhibiting HIV integrase in a subject in need thereof which comprises administering to the subject an effective amount of a compound of Formula I.

(h) A method for the treatment or prophylaxis of infection by HIV in a subject in need thereof which comprises administering to the subject an effective amount of a compound of Formula I.

(i) The method of (h), wherein the compound of Formula I is administered in combination with an effective amount of at least one antiviral selected from the group consisting of HIV protease inhibitors, non-nucleoside HIV reverse transcriptase inhibitors, nucleoside HIV reverse transcriptase inhibitors, and HIV fusion inhibitors.

(j) A method for the treatment, prophylaxis, or delay in the onset of AIDS in a subject in need thereof which comprises administering to the subject an effective amount of a compound of Formula I.

(k) The method of (j), wherein the compound is administered in combination with an effective amount of at least one antiviral selected from the group consisting of HIV protease inhibitors, non-nucleoside HIV reverse transcriptase inhibitors, nucleoside HIV reverse transcriptase inhibitors, and HIV fusion inhibitors.

(l) A method of inhibiting HIV integrase in a subject in need thereof which comprises administering to the subject the pharmaceutical composition of (a), (b), (c) or (d) or the combination of (e) or (f).

(m) A method for the treatment or prophylaxis of infection by HIV in a subject in need thereof which comprises administering to the subject the pharmaceutical composition of (a), (b), (c) or (d) or the combination of (e) or (f).

(n) A method for the treatment, prophylaxis, or delay in the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) the inhibition of HIV integrase, (b) treatment or prophylaxis of infection by HIV, or (c) treatment, prophylaxis, or delay in the onset of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

The present invention also includes prodrugs of the compounds of Formula I. The term "prodrug" refers to a derivative of a compound of Formula I, or a pharmaceutically acceptable salt thereof, which is converted in vivo into Compound I. Prodrugs of compounds of Formula I can exhibit enhanced solubility, absorption, and/or lipophilicity compared to the compounds per se, thereby resulting in increased bioavailability and efficacy. The in vivo conversion of the prodrug can be the result of an enzyme-catalyzed chemical reaction, a metabolic chemical reaction, and/or a spontaneous chemical reaction (e.g., solvolysis). The prodrug can be, for example, a derivative of a hydroxy group such as an ester (—OC(O)R), a carbonate ester (—OC(O)OR), a phosphate ester (—O—P(=O)(OH)$_2$), or an ether (—OR). Other examples include the following: When the compound of Formula I contains a carboxylic acid group, the prodrug can be an ester or an amide, and when the compound of Formula I contains a primary amino group, the prodrug can be an amide, carbamate, imine, or a Mannich base. One or more functional groups in Compound I can be derivatized to provide a prodrug thereof. Conventional procedures for the selection and preparation of suitable prodrug derivatives are described, for example, in *Design of Prodrugs*, edited by H. Bundgaard, Elsevier, 1985; C. S. Larsen and J. Ostergaard, "Design and application of prodrugs" in: *Textbook of Drug Design and Discovery*, 3$^{rd}$ edition, edited by C. S. Larsen, 2002, pp. 410-458; and Beaumont et al., *Current Drug Metabolism* 2003, vol. 4, pp. 461-458; the disclosures of each of which are incorporated herein by reference in their entireties. Prodrugs of compounds of Formula I can also be selected and prepared in accordance with the description in WO 2005/070901, herein incorporated by reference in its entirety.

As used herein, the term "HIV antiviral agent" refers to a substance that can be employed in the treatment or prophylaxis of HIV infection or in the treatment, prophylaxis or delay in the onset of AIDS, wherein the substance (i) directly or indirectly acts to prevent or inhibit HIV infection or its spread or (ii) directly or indirectly acts to prevent or inhibit a secondary viral infection or its spread wherein the secondary viral infection is associated with and/or caused by the HIV infection (e.g., an opportunistic viral infection).

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkylene" refers to any divalent linear or branched chain aliphatic hydrocarbon radical (or alternatively an "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —(CH$_2$)$_{1-6}$—, and sub-classes of particular interest include —(CH$_2$)$_{1-4}$—, —(CH$_2$)$_{1-3}$—, —(CH$_2$)$_{1-2}$—, and —CH$_2$—. Another class of alkylenes of particular interest is an alkylene selected from the group consisting of —CH$_2$—, —CH(CH$_3$)—, and —C(CH$_3$)$_2$—.

The term "C(O)" refers to carbonyl. The terms "S(O)$_2$" and "SO$_2$" each refer to sulfonyl. The term "S(O)" refers to sulfinyl.

The symbol "*" at the end of a bond each refer to the point of attachment of a functional group or other chemical moiety to the rest of the molecule of which it is a part.

The terms "cycloalkyl" refers to any cyclic ring of an alkane having a number of carbon atoms in the specified range. Thus, for example, "C$_{3-8}$ cycloalkyl" (or "C$_3$-C$_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "C$_{1-6}$ haloalkyl" (or "C$_1$-C$_6$ haloalkyl") refers to a C$_1$ to C$_6$ linear or branched alkyl group as defined above with one or more halogen substituents. The term "fluoroalkyl" has an analogous meaning except that the halogen substituents are restricted to fluoro. Suitable fluoroalkyls include the series (CH$_2$)$_{0-4}$CF$_3$ (i.e., trifluoromethyl, 2,2,2-trifluoroethyl, 3,3,3-trifluoro-n-propyl, etc.). Fluoroalkyls of particular interest include CF$_3$, CH$_2$CF$_3$, CH$_2$CH$_2$CF$_3$, CF$_2$CF$_3$, and CH$_2$CF$_2$CF$_3$.

Suitable aryls include phenyl, 9- and 10-membered bicyclic, fused carbocyclic ring systems, and 11- to 14-membered tricyclic fused carbocyclic ring systems, wherein in the fused carbocyclic ring systems at least one ring is aromatic. Suitable aryls include, for example, phenyl, naphthyl, tetrahydronaphthyl (tetralinyl), indenyl, anthracenyl, and fluorenyl. Suitable heteroaryls include 5- and 6-membered heteroaromatic rings and 9- and 10-membered bicyclic, fused ring systems in which at least one ring is aromatic, wherein the heteroaromatic ring or the bicyclic, fused ring system contains from 1 to 4 heteroatoms independently selected from N, O and S, wherein each N is optionally in the form of an oxide and each S in a ring which is not aromatic is optionally S(O) or S(O)$_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. Suitable heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl (e.g., benzo-1,3-dioxolyl:

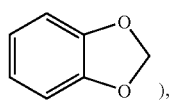), benzopiperidinyl, benzisoxazolyl, benzoxazolyl, chromanyl, isochromanyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl (i.e.,

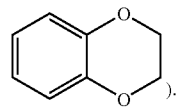).

Suitable saturated and mono-unsaturated heterocyclic rings include 4- to 7-membered saturated and mono-unsaturated heterocyclic rings containing at least one carbon atom and from 1 to 4 heteroatoms independently selected from N, O and S, wherein each S is optionally oxidized to S(O) or S(O)$_2$. Suitable 4- to 7-membered saturated heterocyclics include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Suitable mono-unsaturated heterocyclic rings include those corresponding to the saturated heterocyclic rings listed in the preceding sentence in which a single bond is replaced with a double bond (e.g., a carbon-carbon single bond is replaced with a carbon-carbon double bond). Suitable saturated and mono-unsaturated heterobicyclic rings include 6- to 10-membered saturated and mono-unsaturated, bridged or fused heterobicyclic rings containing from 1 to 4 heteroatoms independently selected from N, O and S, where each S is optionally oxidized to S(O) or S(O)$_2$. Suitable saturated heterobicyclics include:

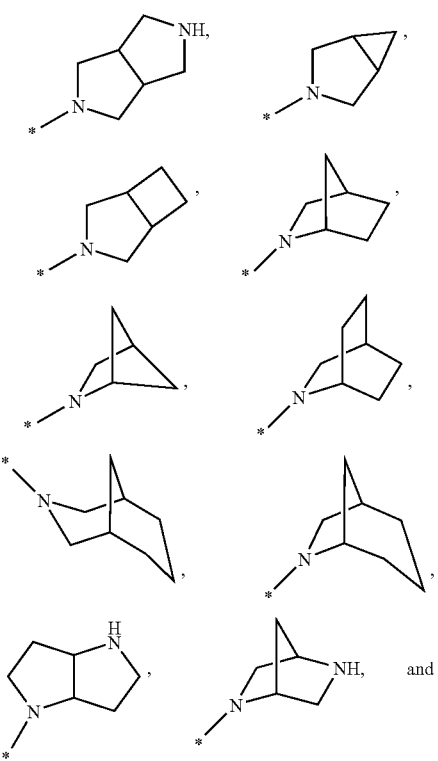

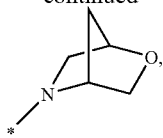

and suitable mono-unsaturated heterobicyclics include those corresponding to the foregoing saturated heterobicyclics in which a single bond is replaced with a double bond. It is understood that the specific rings and ring systems suitable for use in the present invention are not limited to those listed in this paragraph. The rings and ring systems listed in this paragraph are merely representative.

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 to 4 heteroatoms, 1 to 3 heteroatoms, 2 to 3 heteroatoms, 1 to 2 heteroatoms, 1 heteroatom, 2 heteroatoms, 3 heteroatoms, and 4 heteroatoms. As another example, an aryl described as optionally substituted with "from 1 to 5 substituents" is intended to include as aspects thereof, an aryl optionally substituted with 1 to 4 substituents, 1 to 3 substituents, 1 to 2 substituents, 2 to 5 substituents, 2 to 4 substituents, 2 to 3 substituents, 3 to 5 substituents, 3 to 4 substituents, 4 to 5 substituents, 1 substituent, 2 substituents, 3 substituents, 4 substituents, and 5 substituents.

When any variable (e.g., $R^A$, $R^B$, or AryE) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "is optionally substituted with from 1 to 5 substituents . . . ") includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., cycloalkyl, aryl, a heteroaromatic ring, or a saturated heterocyclic ring) provided such ring substitution is chemically allowed and results in a stable compound. Ring substituents can be attached to the ring atom which is attached to the rest of the molecule, provided a stable compound results.

Any of the various carbocyclic and heterocyclic rings and ring systems defined herein may be attached to the rest of the compound at any ring atom (i.e., any carbon atom or any heteroatom) provided that a stable compound results.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers or enantiomers. All isomeric forms of these compounds, whether isolated or in mixtures, are within the scope of the present invention.

As would be recognized by one of ordinary skill in the art, certain of the compounds of the present invention can exist as tautomers. All tautomeric forms of these compounds, whether isolated or in mixtures, are within the scope of the present invention.

In instances where a hydroxy (—OH) substituent is permitted on a heteroaromatic ring and keto-enol tautomerism is possible, it is understood that the substituent might in fact be present, in whole or in part, in the keto form, as exemplified here for a hydroxypyridinyl substituent:

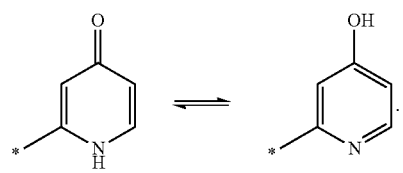

Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

The compounds of the present invention are useful in the inhibition of HIV integrase (e.g., HIV-1 integrase), the prophylaxis or treatment of infection by HIV and the prophylaxis, treatment or the delay in the onset of consequent pathological conditions such as AIDS. The prophylaxis of AIDS, treating AIDS, delaying the onset of AIDS, the prophylaxis of infection by HIV, or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to MW by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention can be commercial products to be sold for these purposes.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Certain compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administered" or "administering") in reference to a compound of the invention mean providing the compound or a prodrug of the compound to the individual in need of treatment or prophylaxis. When a compound of the invention or a prodrug thereof is provided in combination with one or more other active agents (e.g., antiviral agents useful for the prophylaxis or treatment of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (or, alternatively, "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV integrase and thereby elicit the response being sought (i.e., an "inhibition effective amount"). When the active compound (i.e., active ingredient) is administered as the salt, references to the amount of active ingredient are to the free acid or free base form of the compound.

For the purpose of the inhibition of HIV integrase, the prophylaxis or treatment of HIV infection, or the prophylaxis or treatment or delay in the onset of AIDS, the compounds of the present invention, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition, edited by A. R. Gennaro, Mack Publishing Co., 1990.

The compounds of this invention can be administered orally in a dosage range of about 0.001 to about 1000 mg/kg of mammal (e.g., human) body weight per day in a single dose or in divided doses. One preferred dosage range is about 0.01 to about 500 mg/kg body weight per day orally in a single dose or in divided doses. Another preferred dosage range is about 0.1 to about 100 mg/kg body weight per day orally in single or divided doses. For oral administration, the compositions can be provided in the form of tablets or capsules containing about 1.0 to about 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the age, body weight, general health, sex, and diet of the subject undergoing therapy, the activity of the specific compound employed, the metabolic stability and length of action of that compound, the mode and time of administration, rate of excretion, drug combination, and the severity of the particular condition.

As noted above, the present invention is also directed to use of the HIV integrase inhibitor compounds of the present invention with one or more anti-HIV agents useful in the treatment of HIV infection or AIDS. An "anti-HIV agent" is any agent which is directly or indirectly effective in the inhibition of HIV integrase or another enzyme required for HIV replication or infection, the treatment or prophylaxis of HIV infection, and/or the treatment, prophylaxis or delay in the onset of AIDS. It is understood that an anti-HIV agent is effective in treating, preventing, or delaying the onset of HIV infection or AIDS and/or diseases or conditions arising therefrom or associated therewith. For example, the compounds of this invention may be effectively administered, whether at periods of pre-exposure and/or post-exposure, in combination with effective amounts of one or more HIV antiviral agents, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

| Name | Type |
| --- | --- |
| abacavir, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, Retrovir ® | nRTI |
| capravirine | nnRTI |
| ddC, zalcitabine, dideoxycytidine, Hivid ® | nRTI |
| ddI, didanosine, dideoxyinosine, Videx ® | nRTI |
| delavirdine, Rescriptor ® | nnRTI |
| efavirenz, Sustiva ®, Stocrin ® | nnRTI |
| emtricitabine, FTC, Emtriva ® | nRTI |
| emtricitabine + tenofovir disoproxil, Truvada ® | nRTI |
| emvirine, Coactinon ® | nnRTI |
| enteric coated didanosine, Videx EC ® | nRTI |
| enfuvirtide, Fuzeon ® | FI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| nelfinavir, Viracept ® | PI |
| nevirapine, Viramune ® | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir disoproxil fumarate, Viread ® | nRTI |
| tipranavir, Aptivus ® | PI |

FI = fusion inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., indinavir sulfate, atazanvir sulfate, nelfinvavir mesylate.

It will be understood that the scope of combinations of the compounds of this invention with HIV antivirals, immunomodulators, anti-infectives or vaccines is not limited to the foregoing substances in Table A or to the list in the above-referenced Tables in WO 01/38332 and WO 02/30930, but includes in principle any combination with any pharmaceutical composition useful for the treatment of AIDS. The HIV antivirals and other agents are employed in an amount which, in combination with the compounds of the present invention, will be effective in the treatment or prophylaxis of HIV infection and/or in the treatment, prophylaxis, or delay in the onset of AIDS. These agents can be employed in the combinations in their conventional dosage ranges and regimens as reported in the art, including, for example, the dosages described in the *Physicians' Desk Reference*, 58$^{th}$ edition, Thomson PDR, 2004. The dosage ranges for a compound of the invention in these combinations are the same as those set forth above. It is understood that pharmaceutically acceptable salts of the compounds of the invention and/or the other agents (e.g., indinavir sulfate) can be used as well.

Abbreviations employed herein include the following: AcOH=acetic acid; Bn=benzyl; DCM=dichloromethane; DDQ=2,3-dichloro-5,6-dicyano-1,4-benzoquinone; DMAD=dimethylacetylenedicarboxylate; DMSO=dimethylsulfoxide; Et=ethyl; EtOAc=ethyl acetate; i-Bu=isobutyl; Me=methyl; MeOH=methanol; MS=mass spectroscopy; NBS=N-bromosuccinimide; NMR=nuclear magnetic resonance; PE=petroleum ether; n-Pr=n-propyl; Ph=phenyl; RP-HPLC=reverse phase HPLC; TEA=triethylamine; TFA=trifluoroacetic acid.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Scheme A depicts two routes for the synthesis of 3-hydroxy-4-oxo-pyrido[1,2-a]pyrimidine-2-carboxamide A6. In Route 1,2-aminopyridine-N-oxide A1 is reacted with dimethylacetylene dicarboxylate to afford the adduct A2, which can be cyclized with heating to provide methyl 3-hydroxy-4-oxo-pyrido[1,2-a]pyrimidine-2-carboxylate A5-a. The 3-hydroxy group is then protected with a suitable protective group PG to provide methyl ester A5-b, which can be reacted with an amine of formula HN(R$^5$)R$^6$ in a suitable solvent (e.g., DMF, methanol, ethanol, toluene, or NMP) at elevated temperature (e.g. from about 40° C. to about 80° C. depending inter alia upon choice of solvent) to give the desired compound A6. Alternatively in Route 2, methyl-3-hydroxy-4-oxo-6,7,8,9-tetrahydro-4H-pyrido[1,2-a]pyrimidine-2-carboxylate A3 (which can be prepared as described in WO 2004/058756 A1) is reacted with DDQ and then treated with a base (e.g., a trialkyl amine such as triethylamine) to afford unsaturated intermediate A4. The dihydro intermediate A4 can be further dehydrogenated by heating in the presence of a dehydrogenation catalyst (e.g., Pd on charcoal) to give A5 which can be coupled with amine HN(R$^5$)R$^6$ without isolation to afford A6.

Suitable OH-protective groups and methods for their introduction and removal are described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991. Methods for coupling esters with amines to form carboxamides are well known in the art. Suitable methods are described, for example, in Jerry March, *Advanced Organic Chemistry*, 3rd edition, John Wiley & Sons, 1985, pp. 375-376 and references cited therein, and in Richard Larock, *Comprehensive Organic Transformations*, VCH Publishers Inc, 1989, pp 987-988. Amines of formula HN(R$^5$)R$^6$ can be prepared using the methods described in Richard Larock, *Comprehensive Organic Transformations*, VCH Publishers Inc, 1989, pp 385-438, or routine variations thereof.

Scheme A

Route 1

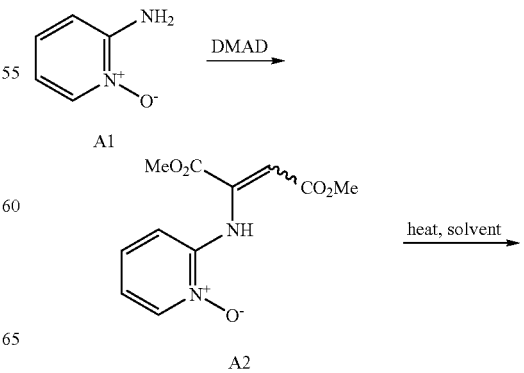

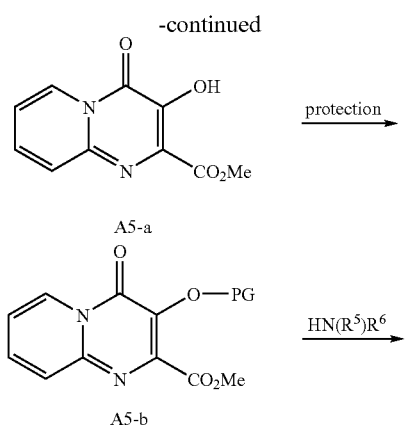

A5-a

A5-b

[PG = protective group]

Route 2

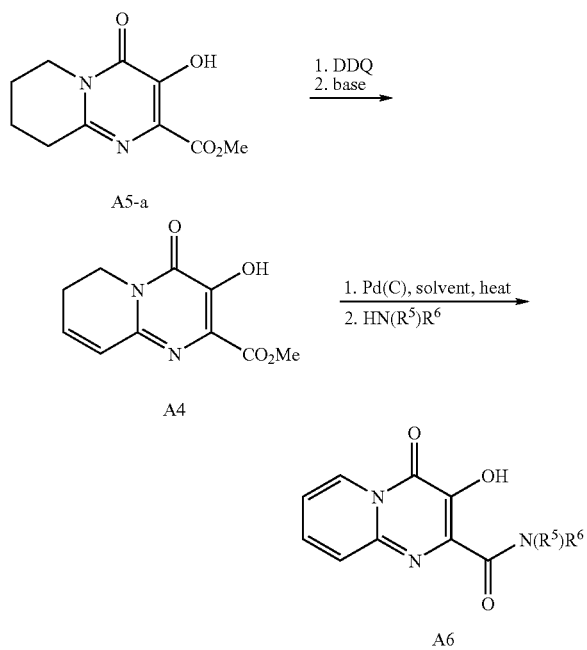

A5-a

A4

A6 with an amine of formula $HN(R^5)R^6$ to provide carboxamide B3. After deprotection of the amino group in B3, the resulting primary amine B4 can be transformed into a secondary or tertiary amine by a reductive alkylation or it can be transformed into secondary amide by acylation with an activated ester or an acyl halide. Tertiary amides can be obtained by first subjecting B4 to a reductive mono-alkylation and then to acylation with a suitable carboxylic acid derivative.

Alternatively in Route 2, B5' can be obtained by a dehydrogenation reaction of the advanced intermediate B4' (which can be prepared in the manner described in WO 2004/058756 A1). The same transformations applied to B4 in Route 1 can be applied to B5' to give the final product B5.

Scheme B

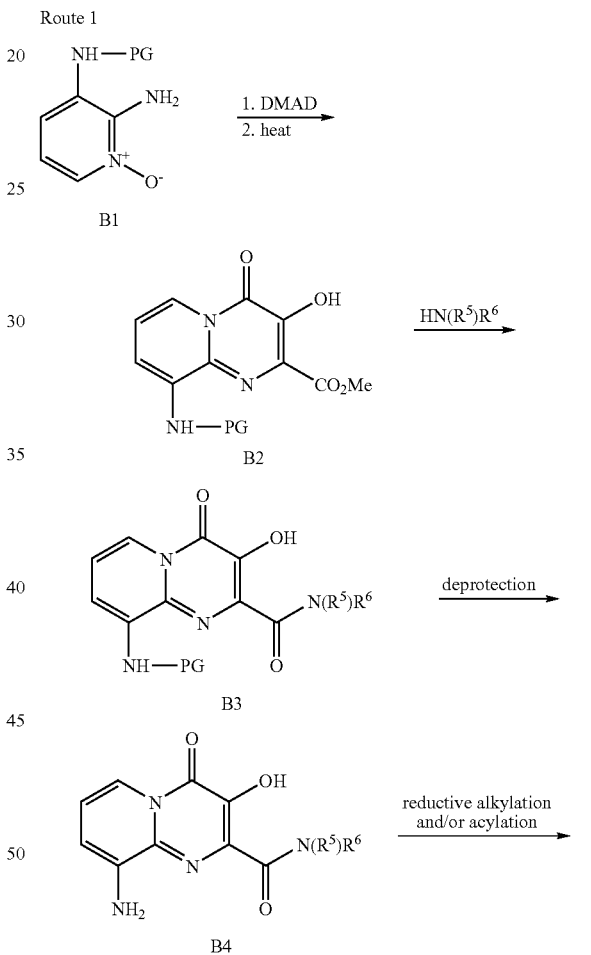

Scheme B shows two routes for the preparation of compounds of the present invention bearing an amino- or an amide-functionality at the 9-position. In Route 1,3-N-protected 2,3-diaminopyridine-N-oxide B1 is reacted with dimethylacetylene dicarboxylate to form an adduct which is transformed by heating and without isolation into methylcarboxylate B2 having a protected amino group at the 9-position. (Suitable amine-protective groups and methods for their introduction and removal are described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3rd edition, 1999, and 2nd edition, 1991.) The methyl ester B2 can be reacted

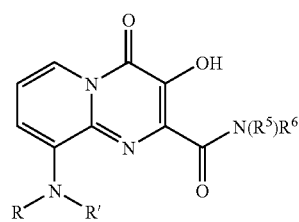

B5

[PG = protective group]

29

-continued

Route 2

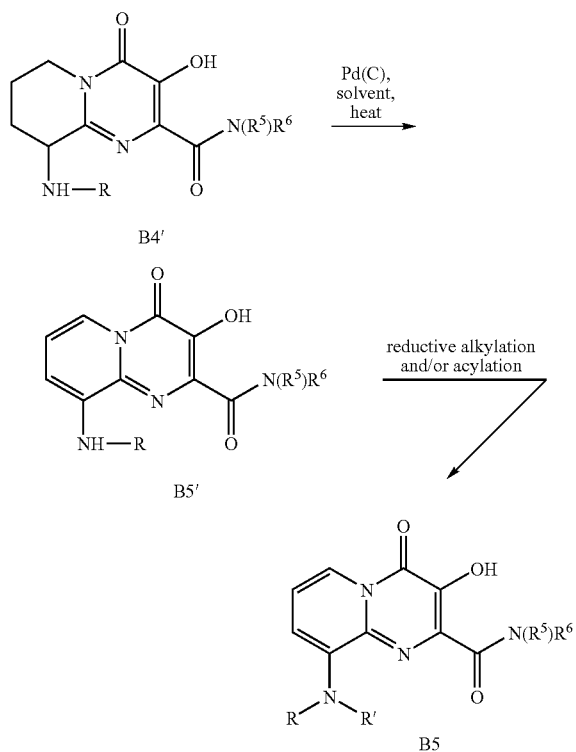

[R = H or lower alkyl,
R' = lower alkyl or an acyl group such as —C(O)R* or C(O)C(O)R^, where R* is alkyl, cycloalkyl, aryl, heteroaryl, O-alkyl, O-cycloalkyl, O-aryl, O-heteroaryl, amino, alkylamino, dialkylamino, or the like; and R^ is amino, alkylamino, dialkylamino, or the like.]

Scheme C shows a method for preparing compounds of the present invention that contain an alkyl-, alkoxy-, aminomethyl- or an amidomethyl-substituent at the 9-position of the pyrido[1,2-a]pyrimidine. 3-Alkyl- or 3-alkoxy-substituted 2-aminopyridine-N-oxide C1 is reacted with DMAD to give adduct C2, which can be cyclized by heating to provide C3. The methyl ester C3 can then be reacted with an amine of formula $HN(R^5)R^6$ to give carboxamide C4. When C4 has a methyl, ethyl, or benzyl group in the 9-position (note: R" is methyl in Scheme C), C4 can be brominated (with, e.g., NBS) and the resulting bromide reacted with an amine to afford C5, which has an aminomethyl group at the 9-position. When C5 is a primary or secondary amine, the amine can be acylated to provide amide C6.

Scheme C

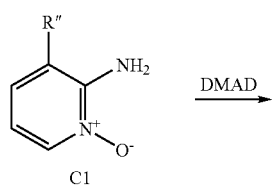

30

-continued

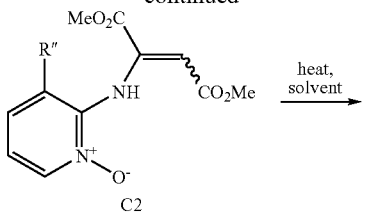

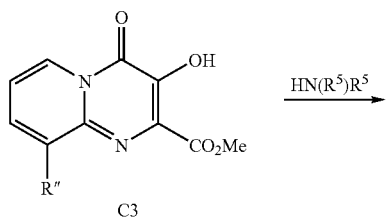

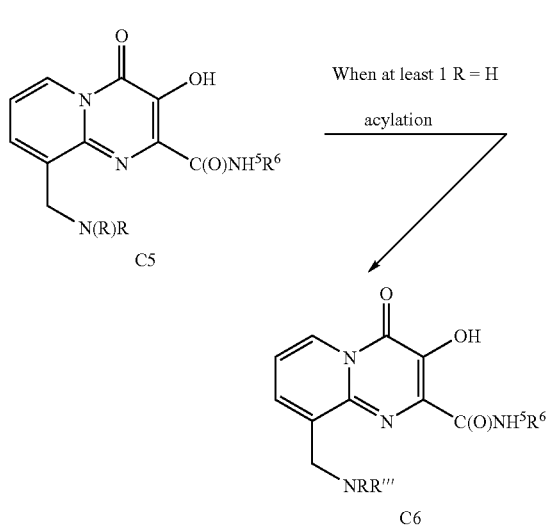

R = H or lower alkyl,
R" = lower alkyl alkoxy
R''' = acyl group such as C(O)R* or C(O)C(O)R^ as defined in Scheme B Scheme D is a method for preparing compounds of the present invention bearing a bromo, aryl, or heteroaryl substituent in the 7-position. Intermediate A5 can be selectively brominated in the 7-position by sequential treatment with NBS in acetic acid and then with triethylamine. The resulting bromo-derivative D1 can then be reacted with an amine of formula $HN(R^5)R^6$ to give the carboxamide D2. Alternatively, the bromine of D1 can be displaced using a palladium-mediated coupling reaction such as Suzuki-coupling to obtain methyl ester D3, which can then be reacted with an amine of formula $HN(R^5)R^6$ to give the carboxamide D4.

31

Scheme D

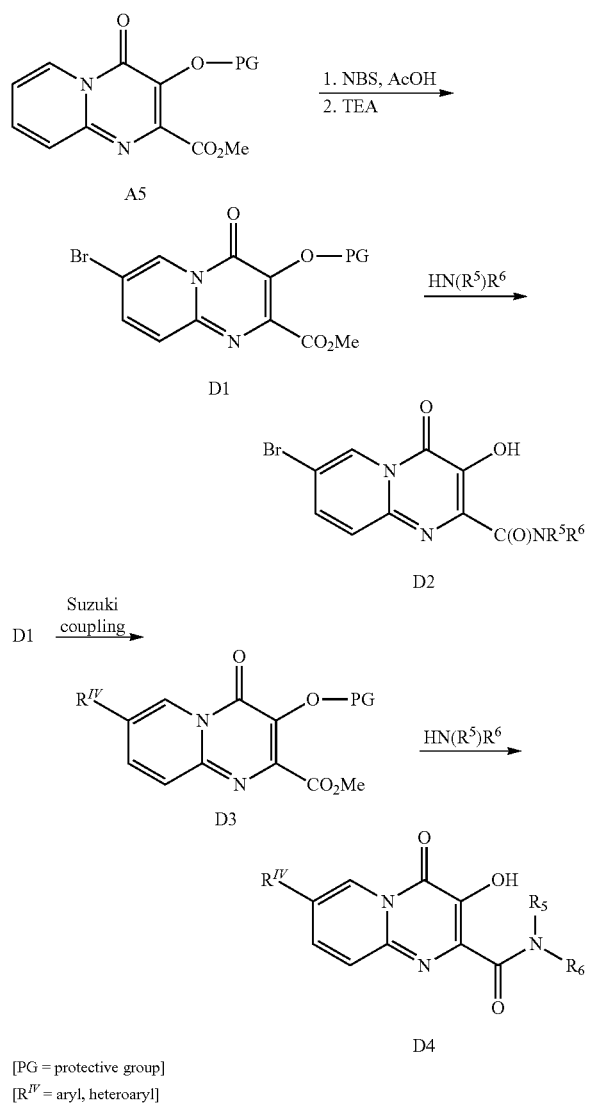

[PG = protective group]
[R$^{IV}$ = aryl, heteroaryl]

The following examples serve only to illustrate the invention and its practice. The examples are not to be construed as limitations on the scope or spirit of the invention. As used herein, the term "equivalent(s)" (=eq(s).) means a molar equivalent.

Example 1

N-(4-Fluorobenzyl)-3-hydroxy-4-oxo-4H-pyrido[1,2-a]pyrimidine-2-carboxamide

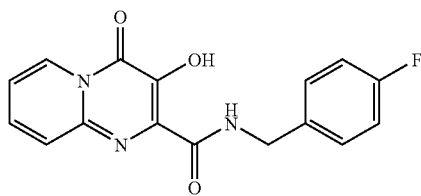

32

Step 1a: Dimethyl (2Z)-2-[(1-oxidopyridin-2-yl)amino]fumarate

To a stirred solution of 2-aminopyridine-N-oxide in chloroform at 0° C. was added dropwise a solution of DMAD (1 eq.) in chloroform. After addition the cooling bath was removed and stirring was continued for 1 hour. A further 0.2 eq. of DMAD was added and stirring continued for 1 hour. The solution was filtered over a silica gel plug. After elution with EtOAc/PE (4:6), the product was eluted with MeOH/EtOAc. The combined MeOH/EtOAc-phases were concentrated to dryness. The title compound was obtained as a brown oil, which was used without further purification.

$^1$H-NMR (300 MHz, DMSO-d$_6$) δ: 10.49 (s, 1H), 8.26 (m, 1H), 7.31 (m, 1H), 7.03 (m, 2H), 5.70 (s, 1H), 3.78 (s, 3H), 3.71 (s, 3H). $^{13}$C-NMR (125 MHz, DMSO-d$_6$) δ: 167.4, 162.7, 144.3, 142.5, 137.9, 126.9, 118.6, 113.9, 98.9. MS m/z: 253 (M+H)$^+$.

Step 2a: Methyl 3-[(pivaloyl)oxy]-4-oxo-4H-pyrido[1,2-a]pyrimidine-2-carboxylate Dimethyl (2Z)-2-[(1-oxidopyridin-2-yl)amino]fumarate from step 1a was suspended in dry o-xylene and the suspension was stirred and heated to 150-154° C. After 1 hour at 150-154° C. the temperature was raised to 165° C. After 2 hours the solution was left cooling to room temperature. The solvent was removed under reduced pressure and the residue was dissolved in pyridine. Pivaloyl chloride (1 eq.) was added and the mixture was stirred for 2 hours at room temperature. The solvent was removed under reduced pressure and the residue was partitioned between ethyl acetate and 0.6 M aqueous HCl. The aqueous phase was extracted with EtOAc. The combined organic phases were washed with water, brine, dried over Na$_2$SO$_4$ and filtered. The filtrate was concentrated to dryness under reduced pressure and redissolved in dichloromethane. This solution was applied on a silica gel plug. The plug was washed with PE/EtOAc and the product was eluted with EtOAc. The product fraction was filtered over activated charcoal and concentrated to dryness under reduced pressure. The residue was left under high vacuum for 1 hour. The title compound was obtained as a light brown solid.

$^1$H-NMR (300 MHz, DMSO-d$_6$) δ: 8.92 (d, J=7.8 Hz, 1H), 8.05 (m, 1H), 7.84 (d, J=7.5 Hz, 1H), 7.48 (m, 1H), 3.88 (s, 3H), 1.32 (s, 9H). (1594-157). $^{13}$C-NMR (75 MHz, DMSO-d$_6$) δ: 174.8, 163.4, 153.3, 148.1, 144.1, 137.5, 127.8, 127.2, 126.4, 117.5, 52.8, 26.7. MS m/z: 305 (M+H)$^+$. mp (recrystallized from methanol): 149.2° C.

Step 3a: N-(4-Fluorobenzyl)-3-hydroxy-4-oxo-4H-pyrido[1,2-a]pyrimidine-2-carboxamide Methyl 3-[(pivaloyl)oxy]-4-oxo-4H-pyrido[1,2-a]pyrimidine-2-carboxylate was dissolved in methanol. p-Fluorobenzylamine (2 eqs.) was added and the reaction was stirred and heated to 60° C. for 2 hours. A precipitate had formed and further methanol and 1 eq. of triethylamine were added. After 2 more hours at 60° C. the reaction mixture was partitioned between EtOAc and 1 M HCl. The organic phase was extracted with 0.1 M aqueous NaOH. The aqueous phase was separated and acidified with 1 M HCl. The aqueous phase was extracted with EtOAc and the organic phase was dried over Na$_2$SO$_4$, filtered and concentrated to dryness. The title compound was obtained as a yellow solid.

$^1$H-NMR (300 MHz, DMSO-d$_6$) δ: 12.21 (s, 1H), 9.70 (t, J=6.0 Hz, 1H), 8.75 (d, J=7.2 Hz, 1H), 7.68 (m, 1H), 7.54 (d,

J=9.0 Hz, 1H), 7.41 (m, 2H), 7.22-7.13 (m, 3H), 4.52 (d, J=6.4 Hz, 2H). MS m/z: 314 (M+H)+.

Step 1b: Methyl 3-hydroxy-4-oxo-6,7,-dihydro-4H-pyrido[1,2-a]pyrimidine-2-carboxylate To a solution of methyl 3-hydroxy-4-oxo-6,7,8,9-tetrahydro-4H-pyrido[1,2-a]pyrimidine-2-carboxylate in 1,4,-dioxane was added dichloro-dicyano benzoquinone (1.1 eqs.). The mixture was stirred and heated to 60° C. for 1 hour. TEA (5 eqs.) was added and stirring was continued for 4 hours. The solution was cooled to room temperature and the product was purified by preparative RP-HPLC, using water (0.1% TFA) and acetonitrile (0.1% TFA) as eluants (column: C18). The product was obtained after lyophilization of the pooled product fractions as a fluffy white material.
$^1$H-NMR (300 MHz, DMSO-$d_6$) δ: 10.42 (s, 1H), 6.60 (m, 1H), 6.75 (d, J=9.72 Hz, 1H), 4.07 (m, 2H), 3.81 (s, 3H), 2.52-2.40 (m, under solvent signal). MS m/z: 223 (M+H)+.

Step 2b: N-(4-Fluorobenzyl)-3-hydroxy-4-oxo-4H-pyrido[1,2-a]pyrimidine-2-carboxamide Methyl 3-hydroxy-4-oxo-6,7,-dihydro-4H-pyrido[1,2-a]pyrimidine-2-carboxylate and Pd(C) (10%) were stirred under nitrogen in anhydrous o-xylene at reflux for 48 hours. After cooling to room temperature the catalyst was filtered off and washed with methanol. The combined organic solutions were concentrated to dryness under high vacuum. A yellow solid remained, which was dissolved in methanol. p-Fluorobenzylamine was added (3 eqs.) and the mixture was stirred and heated to 65° C. overnight. The solvent was removed under reduced pressure and the product was purified by preparative RP-HPLC, using water (0.1% TFA) and acetonitrile (0.1% TFA) as eluants (column: C18). The product was obtained after lyophilization of the pooled product fractions as bright yellow fluffy material. The analytical data were identical to those of the product obtained in step 3a.

Example 2

N-(4-fluorobenzyl)-3-hydroxy-9-{methyl[(methylsulfonyl)acetyl]amino}-4-oxo-4H-pyrido[1,2-a]pyrimidine-2-carboxamide

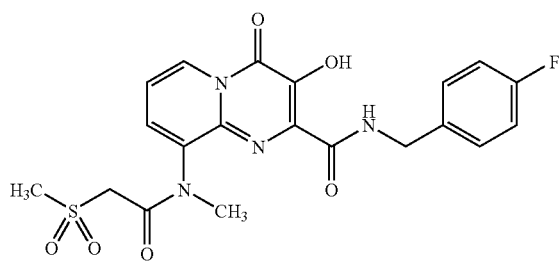

Step 1: N-(4-fluorobenzyl)-3-hydroxy-9-(methylamino)-4-oxo-4H-pyrido[1,2-a]pyrimidine-2-carboxamide To a solution of N-(4-fluorobenzyl)-3-hydroxy-9-(methylamino)-4-oxo-6,7,8,9-tetrahydro-4H-pyrido[1,2-a]pyrimidine-2-carboxamide hydrotrifluoroacetate and diisopropylethylamine (4 eqs.) in o-xylene was added Pd(C) (10%). The suspension was stirred and heated to 156° C. for 7 hours. The suspension was left cooling to room temperature and the catalyst was filtered off. The catalyst was washed with methanol and dichloromethane and the filtrate and catalyst washes were combined and the combined organic solutions were concentrated to dryness. The product was purified by preparative RP-HPLC, using water (0.1% TFA) and acetonitrile (0.1% TFA) as eluants (column: C18). After lyophilization of the pooled product fractions the product was obtained as bright yellow fluffy material.
$^1$H-NMR (300 MHz, CD$_3$CN) δ: 12.04 (s, br, 1H), 8.93 (br, 1H), 8.09 (d, J=6.8 Hz, 1H), 7.43 (m, 2H), 7.11 (m, 2H), 6.99 (m, 1H), 6.39 (d, J=7.3 Hz, 1H), 4.63 (d, J=6.63 Hz, 2H), 2.94 (s, 3H). MS m/z: 343 (M+H)+.

Step 2: N-(4-Fluorobenzyl)-3-hydroxy-9-{methyl[(methylsulfonyl)acetyl]amino}-4-oxo-4H-pyrido[1,2-a]pyrimidine-2-carboxamide N-(4-fluorobenzyl)-3-hydroxy-9-(methylamino)-4-oxo-4H-pyrido[1,2-a]pyrimidine-2-carboxamide was dissolved in dichloromethane. Methylsulfonylacetyl chloride (1.2 eqs.) and triethylamine (2 eqs.) were added and the solution was stirred at room temperature. After 5 hours a further 2 eqs. of methylsulfonylacetyl chloride and 2 eqs. of triethylamine were added. The solvent was removed under vacuum and the residue was suspended in methano/0.1 M NaOH. The suspension was sonicated for 2 minutes and left stirring at room temperature for 30 minutes. The product was purified by preparative RP-HPLC, using water (0.1% TFA) and acetonitrile (0.1% TFA) as eluants (column: C18). The product was obtained after lyophilization of the pooled product fractions as bright yellow fluffy material.
$^1$H-NMR (300 MHz, CD$_3$CN) δ: 12.33 (s, br, 0.3H), 12.28 (s, br, 0.7H), 9.15 (br, 0.3H), 8.75 (m, 1H), 8.53 (br, 0.7H), 7.68 (m, 0.7H), 7.51 (m, 0.3H), 7.41 (m, 2H), 7.10 (m, 3H), 4.69 (d, J=14.4 Hz, 0.3H), 4.59 (d, J=6.42, 2H), 4.14 (d, J=14.4 Hz, 0.3H), 3.91 (d, J=15.5 Hz, 0.7H), 3.80 (d, J=15.5 Hz, 0.7H), 3.44 (s, 0.9H), 3.23 (s, 2.1H), 3.06 (s, 2.1H), 2.94 (s, 0.9H). MS m/z: 463 (M+H)+.

Example 3

N-(4-fluorobenzyl)-3-hydroxy-9-[(N,N,N'-triethyl)-ethanediamide]-4-oxo-4H-pyrido[1,2-a]pyrimidine-2-carboxamide

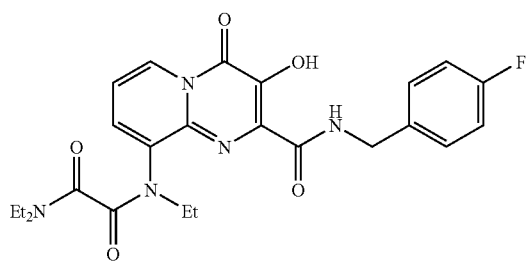

Step 1: Benzyl (2-aminopyridin-3-yl)carbamate

To a solution of 2,3-diaminopyridine in tetrahydrofuran/pyridine (10/1) at 0° C. benzylchloroformate was added dropwise. The suspension was stirred at room temperature and after 2 hours partitioned between water and EtOAc. The organic phase was separated and the aqueous phase was extracted with EtOAc. The combined organic phases were dried over sodium sulfate and the filtrate concentrated to dryness under reduced pressure. To the residue was added Et₂O-MeOH and the solid was filtered.

¹H-NMR (300 MHz, DMSO) δ: 8.79 (s, br, 1H), 7.74 (d, J=4.8 Hz, 1H), 7.61 (d, J=7.5 Hz, 1H), 7.35-7.43 (m, 5H), 6.56 (dd, J=7.5, 4.8 Hz, 1H), 5.76 (s, br, 2H), 5.15 (s, 2H). MS m/z: 244 (M+H)⁺.

Step 2: Benzyl (2-amino-1oxidopyridin-3-yl)carbamate

To a solution of benzyl (2-aminopyridin-3-yl)carbamate in acetone was added a solution of m-chloro perbenzoic acid in acetone and the suspension was stirred at room temperature. After 2 hours the suspension was cooled to 0° C., HCl (2N in Et₂O) was added, and the precipitate filtered. To the precipitate was added saturated aqueous NaHCO₃, EtOAc and MeOH and the mixture stirred until dissolution. The solution was evaporated and the residue washed with water until the pH of the filtrate was neutral. The solid was dried under vacuum.

¹H-NMR (400 MHz, DMSO) δ: 9.12 (s, br, 1H), 7.92 (d, J=6.3 Hz, 1H), 7.44-7.36 (m, 6H), 6.73 (s, 2 H), 6.61 (m, 1H), 5.17 (s, 2H). MS m/z: 260 (M+H)⁺.

Step 3: Methyl 9-{[(benzyloxy)carbonyl]amino}-3-hydroxy-4-oxo-4-H-pyrido[1,2-a]pyrimidine-2-carboxylate To a solution of benzyl (2-amino-1-oxidopyridin-3-yl)carbamate in chloroform (filtered over alumina) was added DMAD and p-toluenesulfonic acid. The suspension was stirred at 70° C. for 12 hours. The solvent was then removed under reduced pressure and to the residue was added MeOH. The solid was filtered, washed with MeOH and dried under vacuum.

¹H-NMR (400 MHz, CD₃CN) δ: 9.95 (s, br, 1H), 8.68 (s, br, 1H), 8.43 (d, J=7.3 Hz, 1H), 8.19 (d, J=7.2 Hz, 1H), 7.51-7.43 (m, 4H), 7.12 (m, 1H), 5.3 (s, 2H), 4.04 (s, 3H). MS m/z: 370 (M+H)⁺.

Step 4: Benzyl (2-{[(4-fluorobenzyl)amino]carbonyl}-3-hydroxy-4-oxo-4H-pyrido[1,2-a]pyrimidin-9-yl)carbamate To a suspension of methyl 9-{[(benzyloxy)carbonyl] amino}-3-hydroxy-4-oxo-4-H-pyrido[1,2-a]pyrimidine-2-carboxylate in MeOH was added p-fluorobenzylamine. The suspension was stirred at 80° C. and after 16 hours the solvent was removed under reduced pressure. The product was purified by preparative RP-HPLC, using water (0.1% TFA) and acetonitrile (0.1% TFA) as eluants (column: C18). The product was obtained after lyophilization of the pooled product fractions as bright yellow fluffy material.

¹H-NMR (400 MHz, DMSO) δ: 12.45 (s, 1H), 10.44 (s, br, 1H), 10.02 (s, 114), 8.45 (d, J=7.1 Hz, 1H), 8.24 (d, J=7.5 Hz, 1H), 7.48-7.38 (m, 6H), 7.18 (m, 314), 5.29 (s, 2H), 4.61 (s, br, 2H). MS m/z/z: 463 (M+H)⁺.

Step 5: N-(4-fluorobenzyl)-3-hydroxy-9-(ethylamino)-4-oxo-4H-pyrido[1,2-a]pyrimidine-2-carboxamide To a solution of benzyl (2-{[(4-fluorobenzyl)amino]carbonyl}-3-hydroxy-4-oxo-4H-pyrido[1,2-a]pyrimidin-9-yl)carbamate in acetic acid was added HBr (30% in AcOH). The solution was stirred at room temperature for 2 hours and afterwards the solvent was removed under reduced pressure. The residue was dissolved several times in toluene and the solvent removed under reduced pressure. The resulting solid was dissolved in 1,2-dichloroethane-MeOH (1:1), acetaldehyde and sodium cyanoborohydride were added, and the mixture stirred at room temperature. After 30 minutes the solvent was removed under reduced pressure and the residue washed with H₂O.

¹H-NMR (400 MHz, DMSO) δ: 12.19 (s, 1H), 10.05 (s, br, 1H), 8.03 (d, J=6.9 Hz, 1H), 7.41 (m, 2H), 7.20 (m, 2H), 7.04 (m, 1H), 6.50 (d, J=7.4 Hz, 1H), 4.62 (d, J=6.0 Hz, 2H), 3.3 (m, 2H), 1.24 (t, J=6.8 Hz, 3H). MS m/z: 356 (M+H)⁺.

Step 6: N-(4-fluorobenzyl)-3-hydroxy-9-[(N,N,N'-triethyl)-ethanediamide]-4-oxo-4H-pyrido[1,2-a] pyrimidine-2-carboxamide To a solution of N-(4-fluorobenzyl)-3-hydroxy-9-(ethylamino)-4-oxo-4H-pyrido[1,2-a]pyrimidine-2-carboxamide in 1,2-dichloroethane was added N,N-(diethylamino)(oxo) acetyl chloride. The mixture was heated to 80° C. and after 2 hours the solvent removed under reduced pressure. The product was purified by preparative RP-HPLC, using water (0.1% TFA) and acetonitrile (0.1% TFA) as eluants (column: C18). The product was obtained after lyophilization of the pooled product fractions as bright yellow fluffy material.

The ¹H-NMR spectrum shows the presence of two conformers in a ratio of 3:2.

¹H-NMR (400 MHz, CD₃CN) δ: 12.48 (s, br, 0.5H), 12.08 (s, br, 0.4H), 9.63 (s, br, 0.4H), 8.74 (d, J=7.41 Hz, 0.4H), 8.59 (s, br, 0.6H), 7.64 (d, J=6.9 Hz, 0.4H), 7.59 (d, J=6.9 Hz, 0.6H), 7.48 (t, br, 0.8H), 7.42 (t, br, 1.2H), 7.13-7.06 (m, 3H), 4.68-4.56 (m, 2H), 4.43 (m, 0.6H), 3.5-3.42 (m, 4H), 3.23 (m, 0.4H), 2.91-2.83 (m, 1H), 1.20 (t, J=6.9 Hz, 1.5H), 1.11 (t, J=6.5 Hz, 1.5H), 0.9 (t, J=6.8 Hz, 1.5H), 0.58 (t, J=6.9 Hz, 1.5H). MS m/z: 484 (M+H)⁺.

Example 4

N-(4-fluorobenzyl)-3-hydroxy-9-(benzyloxy)-4-oxo-4H-pyrido[1,2-a]pyrimidine-2-carboxamide

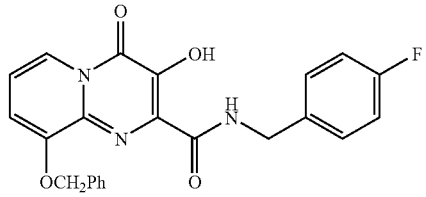

Step 1: 3-(Benzyloxy)pyridin-2-amine 1-oxide

To a solution of 3-(benzyloxy)-2 amine pyridine in acetone was added a solution of m-chloroperbenzoic acid in acetone and the suspension stirred at room temperature. After 1 hour the suspension was cooled to 0° C., HCl (2N in Et₂O) was added, and the precipitate filtered. The solid was then dissolved in DCM, NaHCO₃ added, and the organic phase separated. The aqueous phase was extracted with DCM and the combined organic phases dried over sodium sulfate and filtered. The filtrate was concentrated to dryness under reduced pressure.

¹H-NMR (400 MHz, DMSO) δ: 7.69 (d, J=8.1 Hz, 1H), 7.41 (d, J=7.1 Hz, 2H), 7.38-7.32 (m, 3H), 6.96 (d, J=8.1 Hz, 1H), 6.54 (dd, J=8.1, 8.1 Hz, 1H), 6.48 (s, br, 2H), 5.21 (s, 2H). MS m/z: 217 (M+H)⁺.

Step 2: Methyl 9-(benzyloxy)-3-hydroxy-4-oxo-4H-pyrido[1,2-a]pyrimidine-2-carboxylate To a solution of 3-(benzyloxy)pyridin-2-amine 1-oxide in chloroform was added DMAD. The solution was stirred at room temperature for 8 hours. The solvent was removed under reduced pressure and the residue dissolved in xylene. The xylene solution was stirred and heated to 160° C. and after 8 hours the solvent was removed under reduced pressure. The residue was dissolved in pyridine, benzoic anhydride was added, and the solution stirred at room temperature. After 18 hours the solvent was removed under reduced pressure and the residue was partitioned between EtOAc and HCl (1N). The organic phase was separated, the aqueous phase extracted with ethylacetate, and the combined organic phases dried over sodium sulfate. The filtrate was concentrated to dryness under reduced pressure and the residue purified over silica gel. After elution with EtOAc/PE (6:4), the combined fractions were concentrated to dryness.

¹H-NMR (400 MHz, DMSO) δ: 8.59 (d, J=6.7 Hz, 1H), 8.13 (d, J=7.3 Hz, 2H), 7.80 (t, J=7.4 Hz, 1H), 7.65 (t, J=7.7 Hz, 2H), 7.58-7.46 (m, 3H), 7.45-7.31 (m, 4H), 5.39 (s, 2H), 3.80 (s, 3H). MS m/z: 431 (M+H)⁺.

Step 2: N-(4-Fluorobenzyl)-3-hydroxy-9-(benzyloxy)-4-oxo-4H-pyrido[1,2-a]pyrimidine-2-carboxamide To a solution of methyl 9-(benzyloxy)-3-hydroxy-4-oxo-4H-pyrido[1,2-a]pyrimidine-2-carboxylate in MeOH was added p-fluorobenzylamine. The solution was stirred at 80° C. for 24 hours. The solvent was removed under reduced pressure and the residue washed with diethylether. The product was purified by preparative RP-HPLC, using water (0.1% TFA) and acetonitrile (0.1% TFA) as eluants (column: C18). The product was obtained after lyophilization of the pooled product fractions as bright yellow fluffy material.

¹H-NMR (400 MHz, DMSO) δ: 12.06 (s, 1H), 9.07 (s, br, 1H), 8.38 (d, J=6.6 Hz, 1H), 7.48 (d, J=6.1 Hz, 2H), 7.40-7.31 (m, 5H), 7.19-7.09 (m, 4H), 5.35 (s, 2H), 4.56 (d, J=5.6 Hz, 1H). MS m/z: 420 (M+H)⁺.

Example 5

N-4-fluorobenzyl-3-hydroxy-7-(2-morpholin-4-ylphenyl)-4-oxo-4H-pyrido[1,2-a]pyrimidine-2-carboxamide

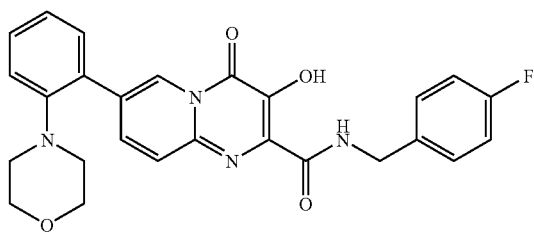

Step 1: Methyl 7-bromo-3-[(2,2-dimethylpropanoyl)oxy]-4-oxo-4H-pyrido[1,2-a]pyrimidine-2-carboxylate Methyl 3-[(pivaloyl)oxy]-4-oxo-4H-pyrido[1,2-a]pyrimidine-2-carboxylate (see Example 1, Step 2a) and NBS (5 eqs.) were dissolved in a 3:1 mixture of acetonitrile and acetic acid. The solution was left standing at 5° C. with occasional shaking for 4 days. The solvents were removed under reduced pressure and the residue was suspended in chloroform. The precipitate was removed by filtration and the solution concentrated under vacuum. The residue was dissolved in dichloromethane, and triethylamine (7 eqs.) was added. The mixture was stirred for 1.5 hours at room temperature, the solvent removed under vacuum, and the residue partitioned between EtOAc and 1N aqueous HCl. The organic phase was washed with 1N aqueous HCl and the combined aqueous phases extracted with EtOAc. The combined organic phases were washed with water, dried over Na₂SO₄, filtered and concentrated under reduced pressure. The product was isolated by flash chromatography (SiO₂, eluant: PE/EtOAc, 4.5:5.5). The product was obtained as a light yellow solid.

¹H-NMR (300 MHz, CDCl₃) δ: 9.03 (s, 1H), 7.68 (m, 2H), 3.92 (s, 3H), 1.38 (s, 9H). MS m/z: 385 (M+H)⁺.

Step 2: N-(4-Fluorobenzyl)-3-hydroxy-7-(2-morpholin-4-ylphenyl)-4-oxo-4H-pyrido[1,2-a]pyrimidine-2-carboxamide Methyl-7-bromo-3-[(2,2-dimethylpropanoyl)oxy]-4-oxo-4H-pyrido[1,2-a]pyrimidine-2-carboxylate, (2-morpholin-4-ylphenyl)boronic acid (1.5 eqs.), palladium(II)-acetate (10 mol %), dicyclohexyl(2',6'-dimethoxybiphenyl-2-yl)phosphine (2.5 eqs. over catalyst), and anhydrous potassium phosphate were placed in a flask under argon and degassed n-butanol was added. The suspension was heated with stirring to 90° C. for 10 minutes. The mixture was diluted with dichloromethane and washed with saturated aqueous NaHCO₃. The organic phase was dried over Na₂SO₄, filtered and concentrated to dryness under reduced pressure. The crude product was dissolved in methanol and p-fluorobenzylamine was added (8 eqs). The mixture was stirred at 65° C. for 5 hours. The crude product was purified by preparative HPLC using water (0.1% TFA) and acetonitrile (0.1% TFA) as eluants (column: C18). The product was obtained after lyophilization of the pooled product fractions as bright yellow solid.

¹H-NMR (400 MHz, DMSO-d₆) δ: 12.23 (s, br, 1H), 9.72 (t, J=6.0, 1H), 8.89 (s, 1H), 8.09 (d, J=8.0 Hz, 1H), 7.57 (d, J=8.0 Hz, 1H), 7.50-7.32 (m, 4H), 7.22-7.11 (m, 4H), 4.53 (d, J=6.0, 2H), 3.52 (s, br, 4H), 2.82 (s, br, 4H). MS m/z: 475 (M+H)⁺.

Examples 6-35

The compounds in Table B below were prepared using a procedure similar to that employed in Example 1. The table provides the structure and name of each compound and the mass of its molecular ion plus 1 (M+1) as determined via MS. When the compound was prepared as a salt, the identity of the salt is included in parentheses following the compound name for the free base. The synthetic scheme employed to prepare the compound is indicated in parentheses following the compound name.

TABLE B

[Structure: pyrido[1,2-a]pyrimidine core with R³ at 7-position, 4-oxo, 3-OH, 2-carboxamide linked to N-H-CH₂-(4-fluorophenyl), and R¹ at 9-position]

| Ex. | Compound (Preparative Method) | R¹ | R³ | M + 1 |
|---|---|---|---|---|
| 6 | 9-[acetyl(methyl)amino]-N-(4-fluorobenzyl)-3-hydroxy-4-oxo-4H-pyrido[1,2-a]pyrimidine-2-carboxamide (B2) | N(Me)C(O)Me | H | 385 |
| 7 | 9-[benzoyl(methyl)amino]-N-(4-fluorobenzyl)-3-hydroxy-4-oxo-4H-pyrido[1,2-a]pyrimidine-2-carboxamide (B1) | N(Me)C(O)-Ph | H | 447 |
| 8 | 9-[methylamino]-N-(4-fluorobenzyl)-3-hydroxy-4-oxo-4H-pyrido[1,2-a]pyrimidine-2-carboxamide (B2) | N(H)Me | H | 343 |
| 9 | 9-[dimethylamino]-N-(4-fluorobenzyl)-3-hydroxy-4-oxo-4H-pyrido[1,2-a]pyrimidine-2-carboxamide (B2) | N(Me)$_2$ | H | 357 |
| 10 | 9-[ethylamino]-N-(4-fluorobenzyl)-3-hydroxy-4-oxo-4H-pyrido[1,2-a]pyrimidine-2-carboxamide (B1) | N(H)Et | H | 357 |
| 11 | N-(2-{[(4-fluorobenzyl)amino]carbonyl}-3-hydroxy-4-oxo-4H-pyrido[1,2-a]pyrimidin-9-yl)-N,N',N'-trimethylethanediamide (B2) | N(Me)C(O)C(O)N(Me)$_2$ | H | 442 |
| 12 | N-(2-{[(4-fluorobenzyl)amino]carbonyl}-3-hydroxy-4-oxo-4H-pyrido[1,2-a]pyrimidin-9-yl)-N-ethyl-N',N'-dimethylethanediamide (B2) | N(Et)C(O)C(O)N(Me)$_2$ | H | 456 |
| 13 | benzyl (2-{[(4-fluorobenzyl)amino]carbonyl}-3-hydroxy-4-oxo-4H-pyrido[1,2-a]pyrimidin-9-yl)carbamate (B1) | N(H)C(O)OBn | H | 463 |
| 14 | 9-[benzoylamino]-N-(4-fluorobenzyl)-3-hydroxy-4-oxo-4H-pyrido[1,2-a]pyrimidine-2-carboxamide (B1) | N(H)C(O)-Ph | H | 433 |
| 15 | 9-[ethyl(isonicotinoyl)amino]-N-(4-fluorobenzyl)-3-hydroxy-4-oxo-4H-pyrido[1,2-a]pyrimidine-2-carboxamide (TFA-salt) (B1) | isonicotinoyl-N(Et)- (4-pyridyl-C(O)-N(Et)-) | H | 576 |
| 16 | 9-[ethyl(pyridin-2-ylcarbonyl)amino]-N-(4-fluorobenzyl)-3-hydroxy-4-oxo-4H-pyrido[1,2-a]pyrimidine-2-carboxamide (TFA-salt) (B1) | (pyridin-2-yl)C(O)-N(Et)- | H | 576 |
| 17 | N-(2-{[(4-fluorobenzyl)amino]carbonyl}-3-hydroxy-4-oxo-4H-pyrido[1,2-a]pyrimidin-9-yl)-N-propyl-N',N'-dimethylethanediamide (B1) | N(n-Pr)C(O)C(O)N(Me)$_2$ | H | 470 |
| 18 | N-(2-{[(4-fluorobenzyl)amino]carbonyl}-3-hydroxy-4-oxo-4H-pyrido[1,2-a]pyrimidin-9-yl)-N-isobutyl-N',N'-dimethylethanediamide (B1) | N(i-Bu)C(O)C(O)N(Me)$_2$ | H | 484 |
| 19 | N-(4-fluorobenzyl)-3-hydroxy-9-{ethyl[morpholin-4-yl(oxo)acetyl]amino}-4-oxo-4H-pyrido[1,2-a]pyrimidine-2-carboxamide (B1) | N(Et)C(O)C(O)-morpholin-4-yl | H | 498 |
| 20 | 9-[(N,N-dimethylglycyl)(ethyl)amino]-N-(4-fluorobenzyl)-3-hydroxy-4-oxo-4H-pyrido[1,2-a]pyrimidine-2-carboxamide (TFA-salt) (B1) | N(Et)C(O)CH$_2$N(Me)$_2$ | H | 556 |
| 21 | 9-[(N,N-diethylglycyl)(ethyl)amino]-N-(4-fluorobenzyl)-3-hydroxy-4-oxo-4H-pyrido[1,2-a]pyrimidine-2-carboxamide (TFA-salt) (B1) | N(Et)C(O)CH$_2$N(Et)$_2$ | H | 584 |

TABLE B-continued

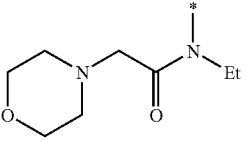

| Ex. | Compound (Preparative Method) | R¹ | R³ | M + 1 |
|---|---|---|---|---|
| 22 | 9-[ethyl(morpholin-4-ylacetyl)amino]-N-(4-fluorobenzyl)-3-hydroxy-4-oxo-4H-pyrido[1,2-a]pyrimidine-2-carboxamide (TFA-salt) (B1) | 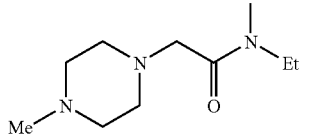 | H | 598 |
| 23 | 9-{ethyl[(4-methylpiperazin-1-yl)acetyl]amino}-N-(4-fluorobenzyl)-3-hydroxy-4-oxo-4H-pyrido[1,2-a]pyrimidine-2-carboxamide (TFA-salt) (B1) | 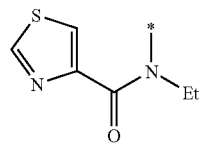 | H | 611 |
| 24 | 9-[ethyl(1,3-thiazol-4-ylcarbonyl)amino]-N-(4-fluorobenzyl)-3-hydroxy-4-oxo-4H-pyrido[1,2-a]pyrimidine-2-carboxamide (B1) | 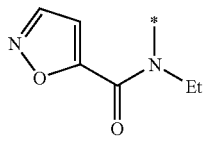 | H | 468 |
| 25 | 9-[ethyl(isoxazol-5-ylcarbonyl)amino]-N-(4-fluorobenzyl)-3-hydroxy-4-oxo-4H-pyrido[1,2-a]pyrimidine-2-carboxamide (B1) | | H | 452 |
| 26 | 9-{ethyl[(5-methyl-1,3,4-oxadiazol-2-yl)carbonyl]amino}-N-(4-fluorobenzyl)-3-hydroxy-4-oxo-4H-pyrido[1,2-a]pyrimidine-2-carboxamide (B1) | 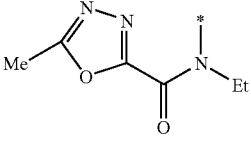 | H | 467 |
| 27 | 9-{ethyl[oxo(pyrrolidin-1-yl)acetyl]amino}-N-(4-fluorobenzyl)-3-hydroxy-4-oxo-4H-pyrido[1,2-a]pyrimidine-2-carboxamide (B1) | 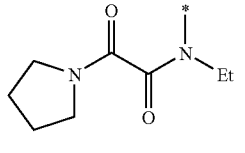 | H | 482 |
| 28 | 4-[[ethyl(2-{[(4-fluorobenzyl)amino]carbonyl}-3-hydroxy-4-oxo-4H-pyrido[1,2-a]pyrimidin-9-yl)amino](oxo)acetyl]-1-methylpiperazine (TFA salt) (B1) | 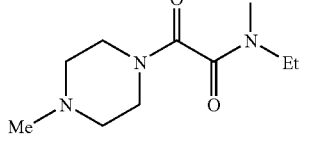 | H | 511 |
| 29 | N-(4-fluorobenzyl)-3-hydroxy-9-methyl-4-oxo-4H-pyrido[1,2-a]pyrimidine-2-carboxamide (C) | Me | H | 328 |
| 30 | 9-[(dimethylamino)methyl]-N-(4-fluorobenzyl)-3-hydroxy-4-oxo-4H-pyrido[1,2-a]pyrimidine-2-carboxamide (TFA-salt) (C) | CH₂N(Me)₂ | H | 485 |
| 31 | N-(4-fluorobenzyl)-3-hydroxy-9-{[methoxy(methyl)amino]methyl}-4-oxo-4H-pyrido[1,2-a]pyrimidine-2-carboxamide (TFA-salt) (C) | CH₂N(Me)OMe | H | 501 |

TABLE B-continued

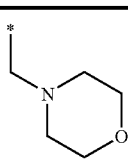

| Ex. | Compound (Preparative Method) | R¹ | R³ | M + 1 |
|---|---|---|---|---|
| 32 | N-(4-fluorobenzyl)-3-hydroxy-9-(morpholin-4-ylmethyl)-4-oxo-4H-pyrido[1,2-a]pyrimidine-2-carboxamide (TFA-salt) (C) | *-CH₂-N(morpholine) | H | 527 |
| 33 | 9-[(4-acetylpiperazin-1-yl)methyl]-N-(4-fluorobenzyl)-3-hydroxy-4-oxo-4H-pyrido[1,2-a]pyrimidine-2-carboxamide (TFA-salt) (C) | *-CH₂-N(piperazine-N-C(O)Me) | H | 568 |
| 34 | 9-[(benzoylamino)methyl]-N-(4-fluorobenzyl)-3-hydroxy-4-oxo-4H-pyrido[1,2-a]pyrimidine-2-carboxamide (C) | CH₂N(H)C(O)-Ph | H | 447 |
| 35 | 7-bromo-N-(4-fluorobenzyl)-3-hydroxy-4-oxo-4H-pyrido[1,2-a]pyrimidine-2-carboxamide (D) | H | Br | 392 |

Example 36

Oral Compositions

As a specific embodiment of an oral composition of a compound of this invention, 50 mg of compound of Example 1 is formulated with sufficient finely divided lactose to provide a total amount of 580 to 590 mg to fill a size 0 hard gelatin capsule. Encapsulated oral compositions containing any one of the compounds of Examples 2 to 35 can be similarly prepared.

Example 37

HIV Integrase Assay

Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds of Examples 1 to 35 were tested in the integrase assay and found to have $IC_{50}$ values of less than about 5 micromolar.

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

Example 38

Assay for Inhibition of HIV Replication

Assays for the inhibition of acute HIV infection of T-lymphoid cells were conducted in accordance with Vacca, J. P. et al., *Proc. Natl. Acad. Sci. USA* 1994, 91: 4096. Representative compounds of the present invention exhibit inhibition of HIV replication in this assay. For example, the compounds set forth in Examples 1-5, 7, 10-13, 16-20 and 24-28 were found to have $IC_{95}$'s of less than 1 micromolar in the assay. The compounds of Examples 6, 8, 9, 14, 15, 21-23 and 29-35 were also tested in the spread assay up to 1 micromolar, but specific $IC_{95}$ values were not obtained; i.e., the $IC_{95}$ values for these compounds are greater than 1 micromolar.

Example 39

Cytotoxicity

Cytotoxicity was determined by microscopic examination of the cells in each well in the spread assay, wherein a trained analyst observed each culture for any of the following morphological changes as compared to the control cultures: pH imbalance, cell abnormality, cytostatic, cytopathic, or crystallization (i.e., the compound is not soluble or forms crystals in the well). The toxicity value assigned to a given compound is the lowest concentration of the compound at which one of the above changes is observed. Representative compounds of the present invention that were tested in the spread assay (see Example 38) were examined for cytotoxicity up to a concentration of 10 micromolar, and no cytotoxicity was exhibited. In particular, the compounds set forth in Examples 1 to 35 exhibited no cytotoxicity at concentrations up to 10 micromolar.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula I, or a pharmaceutically acceptable salt thereof:

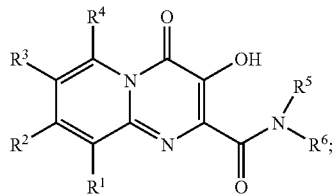

(I)

wherein
$R^1$ and $R^3$ are each independently:
(1) $R^A$,
(2) $R^E$,
(3) $C(O)R^A$,
(4) $C(O)R^E$,
(5) $C(O)OR^A$,
(6) $C(O)OR^E$,
(7) $C(O)N(R^A)R^B$,
(8) $C(O)N(R^A)R^E$,
(9) $OC(O)R^A$,
(10) $OC(O)R^E$,
(11) $OC(O)N(R^A)R^B$,
(12) $OC(O)N(R^A)R^E$,
(13) $N(R^A)R^B$,
(14) $N(R^A)R^E$,
(15) $N(R^A)C(O)R^B$,
(16) $N(R^A)C(O)R^E$,
(17) $N(R^A)C(O)OR^B$,
(18) $N(R^A)C(O)OR^E$,
(19) $N(R^A)C(O)N(R^A)R^B$,
(20) $N(R^A)C(O)N(R^A)R^E$,
(21) $N(R^A)C(O)C(O)N(R^A)R^B$,
(22) $N(R^A)C(O)C(O)N(R^A)R^E$,
(23) $N(R^A)S(O)_2R^B$,
(24) $N(R^A)S(O)_2R^E$,
(25) $N(R^A)S(O)_2N(R^A)R^B$,
(26) $N(R^A)S(O)_2N(R^A)R^E$,
(27) $OR^A$,
(28) $OR^E$,
(29) $SR^A$, $S(O)R^A$, or $S(O)_2R^A$,
(30) $SR^E$, $S(O)R^E$, or $S(O)_2R^E$,
(31) $S(O)_2N(R^A)R^B$,
(32) $S(O)_2N(R^A)R^E$,
(33) CycA, AryA, HetA, or HetR,
(34) $C_{1-6}$ alkyl substituted with CycA, AryA, HetA, or HetR,
(35) J-CycA, J-AryA, J-HetA, or J-HetR,
(36) $C_{1-6}$ alkylene-J-CycA, $C_{1-6}$ alkylene-J-AryA, $C_{1-6}$ alkylene-J-HetA, or $C_{1-6}$ alkylene-J-HetR,
(37) J-$C_{1-6}$ alkylene-CycA, J-$C_{1-6}$ alkylene-AryA, J-$C_{1-6}$ alkylene-HetA, or J-$C_{1-6}$ alkylene-HetR,
(38) $C_{1-6}$ alkylene-J-$C_{1-6}$ alkylene-CycA, $C_{1-6}$ alkylene-J-$C_{1-6}$ alkylene-AryA, $C_{1-6}$ alkylene-J-$C_{1-6}$ alkylene-HetA, or $C_{1-6}$ alkylene-J-$C_{1-6}$ alkylene-HetR, or
(39) halogen;
with the proviso that no more than one of $R^1$ and $R^3$ is other than $R^A$;
$R^2$ and $R^4$ are each $R^A$;
$R^5$ is $R^A$;
$R^6$ is:

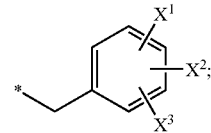

wherein the asterisk * denotes the point of attachment of $R^6$ to the rest of the compound;
$X^1$ and $X^2$ are each independently:
(1) H,
(2) $C_{1-6}$ alkyl,
(3) OH
(4) O—$C_{1-6}$ alkyl,
(5) $C_{1-6}$ haloalkyl,
(6) O—$C_{1-6}$ haloalkyl,
(7) halogen,
(8) CN,
(9) $N(R^A)R^B$,
(10) $C(O)N(R^A)R^B$,
(11) $SR^A$,
(12) $S(O)R^A$,
(13) $SO_2R^A$,
(14) $N(R^A)SO_2R^B$,
(15) $N(R^A)SO_2N(R^A)R^B$,
(16) $N(R^A)C(O)R^B$,
(17) $N(R^A)C(O)C(O)N(R^A)R^B$, or
(18) HetE;
or alternatively $X^1$ and $X^2$ are respectively located on adjacent carbons in the phenyl ring and together form methylenedioxy or ethylenedioxy;
$X^3$ is:
(1) H,
(2) $C_{1-6}$ alkyl,
(3) O—$C_{1-6}$ alkyl,
(4) $C_{1-6}$ haloalkyl,
(5) O—$C_{1-6}$ haloalkyl, or
(6) halogen;
J is:
(1) O,
(2) S,
(3) S(O),
(4) $S(O)_2$,
(5) C(O),
(6) C(O)O,
(7) $C(O)N(R^A)$,
(8) $C(O)N(R^F)$,
(9) $N(R^A)$,
(10) $N(R^F)$,
(11) $N(R^A)C(O)$,
(12) $N(R^F)C(O)$,
(13) $N(R^A)C(O)C(O)$,
(14) $N(R^F)C(O)C(O)$,
(15) $N(R^A)C(O)O$,
(16) $N(R^F)C(O)O$
(17) $N(R^A)S(O)_2$, or
(18) $N(R^F)S(O)_2$;
each $R^A$ is independently H or $C_{1-6}$ alkyl;
each $R^B$ is independently H or $C_{1-6}$ alkyl;
each $R^E$ is independently $C_{1-6}$ haloalkyl or $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)$—O—$C_{1-6}$ alkyl, $N(R^A)C(O)R^B$, $N(R^A)CO_2R^B$, $N(R^A)S(O)_2R^B$, $N(R^A)S(O)_2N(R^A)R^B$, $OC(O)R^A$, $OC(O)N(R^A)R^B$, or $N(R^A)C(O)N(R^A)R^B$;

each $R^F$ is independently $C_{1-6}$ alkyl substituted with CycA, AryA, HetA, or HetR;

each CycA is independently $C_{3-8}$ cycloalkyl which is optionally substituted with a total of from 1 to 6 substituents, wherein:
(i) from zero to 6 substituents are each independently:
(1) halogen,
(2) CN
(3) $C_{1-6}$ alkyl,
(4) OH,
(5) O—$C_{1-6}$ alkyl,
(6) $C_{1-6}$ haloalkyl, or
(7) O—$C_{1-6}$ haloalkyl, and
(ii) from zero to 2 substituents are each independently:
(1) CycE,
(2) AryE,
(3) O-AryE,
(4) HetE,
(5) HetF, or
(6) $C_{1-6}$ alkyl substituted with CycE, AryE, O-AryE, HetE, O-HetE, or HetF;

each AryA is independently aryl which is optionally substituted with a total of from 1 to 6 substituents, wherein:
(i) from zero to 6 substituents are each independently:
(1) $C_{1-6}$ alkyl,
(2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)R^A$, $OC(O)N(R^A)R^B$, $N(R^A)C(O)N(R^A)R^B$, or $N(R^A)C(O)C(O)N(R^A)R^B$,
(3) O—$C_{1-6}$ alkyl,
(4) $C_{1-6}$ haloalkyl,
(5) O—$C_{1-6}$ haloalkyl,
(6) OH,
(7) halogen,
(8) CN,
(9) $NO_2$,
(10) $N(R^A)R^B$,
(11) $C(O)N(R^A)R^B$,
(12) $C(O)R^A$,
(13) $C(O)$—$C_{1-6}$ haloalkyl,
(14) $C(O)OR^A$,
(15) $OC(O)R^A$,
(16) $OC(O)N(R^A)R^B$,
(17) $SR^A$,
(18) $S(O)R^A$,
(19) $S(O)_2R^A$,
(20) $S(O)_2N(R^A)R^B$,
(21) $N(R^A)S(O)_2R^B$,
(22) $N(R^A)S(O)_2N(R^A)R^B$,
(23) $N(R^A)C(O)R^B$,
(24) $N(R^A)C(O)N(R^A)R^B$,
(25) $N(R^A)C(O)$—$C(O)N(R^A)R^B$, or
(26) $N(R^A)CO_2R^B$, and
(ii) from zero to 2 substituents are each independently:
(1) CycE,
(2) O-CycE,
(3) AryE,
(4) O-AryE,
(5) HetE,
(6) O-HetE,
(7) HetF,
(8) O-HetF or
(9) $C_{1-6}$ alkyl substituted with CycE, O-CycE, AryE, O-AryE, HetE, O-HetE, O-HetF, or HetF;

each HetA is independently heteroaryl which is optionally substituted with a total of from 1 to 6 substituents, wherein:
(i) from zero to 6 substituents are each independently:
(1) $C_{1-6}$ alkyl,
(2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)R^A$, $OC(O)N(R^A)R^B$, $N(R^A)C(O)N(R^A)R^B$, or $N(R^A)C(O)C(O)N(R^A)R^B$,
(3) O—$C_{1-6}$ alkyl,
(4) $C_{1-6}$ haloalkyl,
(5) O—$C_{1-6}$ haloalkyl,
(6) OH,
(7) oxo,
(8) halogen,
(9) CN,
(10) $NO_2$,
(11) $N(R^A)R^B$,
(12) $C(O)N(R^A)R^B$,
(13) $C(O)R^A$,
(14) $C(O)$—$C_{1-6}$ haloalkyl,
(15) $C(O)OR^A$,
(16) $OC(O)R^A$,
(17) $OC(O)N(R^A)R^B$,
(18) $SR^A$,
(19) $S(O)R^A$,
(20) $S(O)_2R^A$,
(21) $S(O)_2N(R^A)R^B$,
(22) $N(R^A)S(O)_2R^B$,
(23) $N(R^A)S(O)_2N(R^A)R^B$,
(24) $N(R^A)C(O)R^B$,
(25) $N(R^A)C(O)N(R^A)R^B$,
(26) $N(R^A)C(O)$—$C(O)N(R^A)R^B$, or
(27) $N(R^A)CO_2R^B$, and
(ii) from zero to 2 substituents are each independently:
(1) CycE,
(2) O-CycE,
(3) AryE,
(4) O-AryE,
(5) HetE,
(6) O-HetE,
(7) HetF,
(8) O-HetF or
(9) $C_{1-6}$ alkyl substituted with CycE, O-CycE, AryE, O-AryE, HetE, O-HetE, O-HetF, or HetF;

each HetR is independently (i) a 4- to 7-membered, saturated or mono-unsaturated heterocyclic ring containing at least one carbon atom and from 1 to 4 heteroatoms independently selected from N, O and S, where each S is optionally oxidized to S(O) or $S(O)_2$ or (ii) a 6- to 10-membered saturated or mono-unsaturated, bridged or fused heterobicyclic ring containing from 1 to 4 heteroatoms independently selected from N, O and S, where each S is optionally oxidized to S(O) or $S(O)_2$; and wherein the saturated or mono-unsaturated heterocyclic or heterobicyclic ring is optionally substituted with a total of from 1 to 4 substituents, wherein:
(i) from zero to 4 substituents are each independently halogen, CN, $C_{1-6}$ alkyl, OH, oxo, $C(O)R^A$, $CO_2R^A$, $S(O)R^A$, $SR^A$, $S(O)_2R^A$, O—$C_{1-6}$ alkyl, $C_{1-6}$ haloalkyl, $C_{1-6}$ alkylene-CN, $C_{1-6}$ alkylene-OH, or $C_{1-6}$ alkylene-O—$C_{1-6}$ alkyl; and
(ii) from zero to 2 substituents are each independently CycE, O-CycE, AryE, O-AryE, HetE, O-HetE, HetF, O-HetF, or $C_{1-6}$ alkyl substituted with CycE, O-CycE, AryE, O-AryE, HetE, O-HetE, HetF, O-HetF;

each aryl is independently (i) phenyl, (ii) a 9- or 10-membered bicyclic, fused carbocylic ring system in which at least one ring is aromatic, or (iii) an 11- to 14-membered tricyclic, fused carbocyclic ring system in which at least one ring is aromatic;

each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or $S(O)_2$;

each CycE is independently $C_{3-8}$ cycloalkyl which is optionally substituted with a total of from 1 to 4 substituents, wherein:
  (i) from zero to 4 substituents are each independently halogen, $C_{1-6}$ alkyl, OH, O—$C_{1-6}$ alkyl, $C_{1-6}$ haloalkyl, or O—$C_{1-6}$ haloalkyl, and
  (ii) from zero to 2 substituents are each independently CycG, AryG, HetG, HetH, or $C_{1-6}$ alkyl substituted with CycG, AryG, O-AryG, HetG, or HetH;

each AryE is independently phenyl or naphthyl, wherein the phenyl or naphthyl is optionally substituted with a total of from 1 to 5 substituents, wherein:
  (i) from zero to 5 substituents are each independently halogen, CN, $NO_2$, $C_{1-6}$ alkyl, $C_{1-6}$ haloalkyl, OH, O—$C_{1-6}$ alkyl, O—$C_{1-6}$ haloalkyl, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$, and
  (ii) from zero to 2 substituents are each independently CycG, AryG, HetG, HetH, or $C_{1-6}$ alkyl substituted with CycG, AryG, O-AryG, HetG, or HetH;

each HetE is independently (i) a 5- or 6-membered heteroaromatic ring containing from 1 to 4 heteroatoms independently selected from N, O and S, wherein each N is optionally in the form of an oxide, or (ii) a 9- or 10-membered fused heterobicyclic ring selected from 2,3-dihydrobenzo-1,4-dioxinyl and benzo-1,3-dioxolyl; and wherein the heteroaromatic ring or the heterobicyclic ring is optionally substituted with a total of from 1 to 4 substituents wherein:
  (i) from zero to 4 substituents are each independently halogen, $C_{1-6}$ alkyl, $C_{1-6}$ haloalkyl, O—$C_{1-6}$ alkyl, O—$C_{1-6}$ haloalkyl, OH, $C(O)R^A$, $CO_2R^A$, $SO_2R^A$, $N(R^A)R^B$, $N(R^A)C(O)N(R^A)R^B$, or $N(R^A)CO_2R^B$, and
  (ii) from zero to 2 substituents are each independently CycG, AryG, HetG, HetH, or $C_{1-6}$ alkyl substituted with CycG, AryG, O-AryG, HetG, or HetH;

each HetF is independently a 4- to 7-membered, saturated or mono-unsaturated heterocyclic ring containing at least one carbon atom and from 1 to 4 heteroatoms independently selected from N, O and S, where each S is optionally oxidized to S(O) or $S(O)_2$, and wherein the saturated or mono-unsaturated heterocyclic ring is optionally substituted with a total of from 1 to 4 substituents, wherein:
  (i) from zero to 4 substituents are each independently halogen, CN, $C_{1-6}$ alkyl, OH, oxo, O—$C_{1-6}$ alkyl, $C_{1-6}$ haloalkyl, O—$C_{1-6}$ haloalkyl, $C(O)R^A$, $CO_2R^A$, or $SO_2R^A$, and
  (ii) from zero to 2 substituents are each independently CycG, AryG, HetG, HetH, or $C_{1-6}$ alkyl substituted with CycG, AryG, O-AryG, HetG, or HetH;

each CycG is independently $C_{3-8}$ cycloalkyl which is optionally substituted with from 1 to 4 substituents, each of which is independently halogen, $C_{1-6}$ alkyl, OH, O—$C_{1-6}$ alkyl, $C_{1-6}$ haloalkyl, or O—$C_{1-6}$ haloalkyl;

each AryG is independently phenyl or naphthyl, wherein the phenyl or naphthyl is optionally substituted with from 1 to 5 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$;

each HetG is independently a 5- or 6-membered heteroaromatic ring containing from 1 to 4 heteroatoms independently selected from N, O and S, wherein each N is optionally in the form of an oxide, and wherein the heteroaromatic ring is optionally substituted with from 1 to 4 substituents each of which is independently halogen, $C_{1-6}$ alkyl, $C_{1-6}$ haloalkyl, O—$C_{1-6}$ alkyl, O—$C_{1-6}$ haloalkyl, OH, $C(O)R^A$, $CO_2R^A$, $SO_2R^A$, $N(R^A)R^B$, $N(R^A)C(O)N(R^A)R^B$, or $N(R^A)CO_2R^B$; and each HetH is independently a 4- to 7-membered, saturated or mono-unsaturated heterocyclic ring containing at least one carbon atom and from 1 to 4 heteroatoms independently selected from N, O and S, where each S is optionally oxidized to S(O) or $S(O)_2$, and wherein the saturated or mono-unsaturated heterocyclic ring is optionally substituted with from 1 to 4 substituents, each of which is independently halogen, CN, $C_{1-6}$ alkyl, OH, oxo, O—$C_{1-6}$ alkyl, $C_{1-6}$ haloalkyl, O—$C_{1-6}$ haloalkyl, $C(O)R^A$, $CO_2R^A$, or $SO_2R^A$.

2. The compound according to claim 1, or a pharmaceutically acceptable salt thereof, wherein one of $R^1$ and $R^3$ is:
(1) H,
(2) $C_{1-6}$ alkyl,
(3) $C_{1-6}$ alkyl substituted with $N(R^A)R^B$ or $N(R^A)O—C_{1-6}$ alkyl,
(4) $N(R^A)R^B$,
(5) $N(R^A)C(O)—C_{1-6}$ alkyl, wherein the alkyl is optionally substituted with $N(R^A)R^B$ or $S(O)_2R^A$,
(6) $N(R^A)C(O)C(O)N(R^A)R^B$,
(7) AryA,
(8) HetR,
(9) $C_{1-6}$ alkyl substituted with HetR,
(10) $N(R^A)C(O)C(O)$—HetR,
(11) $N(R^A)C(O)$-AryA,
(12) $N(R^A)C(O)$—HetA,
(13) $N(R^A)C(O)$—HetR,
(14) $N(R^A)C(O)$—$C_{1-6}$ alkylene-AryA,
(15) $N(R^A)C(O)$—$C_{1-6}$ alkylene-HetA,
(16) $N(R^A)C(O)$—$C_{1-6}$ alkylene-HetR,
(17) $C_{1-6}$ alkylene-$N(R^A)C(O)$-AryA,
(18) $C_{1-6}$ alkylene-$N(R^A)C(O)$—HetA,
(19) $N(R^A)C(O)O$—$C_{1-6}$ alkylene-AryA,
(20) $N(R^A)C(O)O$—$C_{1-6}$ alkylene-HetA,
(21) O—$C_{1-6}$ alkylene-AryA,
(22) O—$C_{1-6}$ alkylene-HetA, or
(23) halogen;
and the other of $R^1$ and $R^3$ is H or $C_{1-6}$ alkyl.

3. The compound according to claim 1, or a pharmaceutically acceptable salt thereof, wherein $R^5$ is H.

4. The compound according to claim 1, or a pharmaceutically acceptable salt thereof, wherein $X^1$ and $X^2$ in the definition of $R^6$ are each independently: (1) H, (2) $C_{1-4}$ alkyl, (3) $C_{1-4}$ haloalkyl, (4) OH, (5) O—$C_{1-4}$ alkyl, (6) halogen, (7)

CN, (8) C(=O)NH$_2$, (9) C(=O)NH(—C$_{1-4}$ alkyl), (10) C(=O)N(—C$_{1-4}$ alkyl)$_2$, or (11) SO$_2$—C$_{1-4}$ alkyl; or alternatively X$^1$ and X$^2$ are respectively located on adjacent carbons in the phenyl ring and together form methylenedioxy or ethylenedioxy; and X$^3$ is H, halogen, C$_{1-4}$ alkyl, or O—C$_{1-4}$ alkyl.

5. The compound according to claim 4, or a pharmaceutically acceptable salt thereof, wherein R$^6$ is:

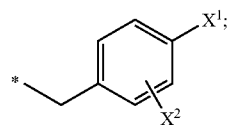

the asterisk * denotes the point of attachment of R$^1$ to the rest of the compound;
X$^1$ is H, bromo, chloro, fluoro, or methoxy; and
X$^2$ is H, bromo, chloro, fluoro, methoxy, C$_{1-4}$ alkyl, CF$_3$, OCF$_3$, CN, or SO$_2$(C$_{1-4}$ alkyl).

6. The compound according to claim 1, or a pharmaceutically acceptable salt thereof, wherein R$^6$ is 4-fluorobenzyl or 3-chloro-4-fluorobenzyl.

7. The compound according to claim 6, or a pharmaceutically acceptable salt thereof, wherein R$^6$ is 4-fluorobenzyl.

8. The compound according to claim 1, or a pharmaceutically acceptable salt thereof, wherein:
R$^1$ is:
   (1) H,
   (2) C$_{1-6}$ alkyl,
   (3) C$_{1-6}$ alkyl substituted with N(R$^A$)R$^B$ or N(R$^A$)O—C$_{1-6}$ alkyl,
   (4) N(R$^A$)R$^B$,
   (5) N(R$^A$)C(O)—C$_{1-6}$ alkyl, wherein the alkyl is optionally substituted with N(R$^A$)R$^B$ or S(O)$_2$R$^A$,
   (6) N(R$^A$)C(O)C(O)N(R$^A$)R$^B$,
   (7) HetR,
   (8) C$_{1-6}$ alkyl substituted with HetR,
   (9) N(R$^A$)C(O)C(O)—HetR,
   (10) N(R$^A$)C(O)-AryA,
   (11) N(R$^A$)C(O)—HetA,
   (12) N(R$^A$)C(O)—HetR,
   (13) N(R$^A$)C(O)—C$_{1-6}$ alkylene-AryA,
   (14) N(R$^A$)C(O)—C$_{1-6}$ alkylene-HetA,
   (15) N(R$^A$)C(O)—C$_{1-6}$ alkylene-HetR,
   (16) C$_{1-6}$ alkylene-N(R$^A$)C(O)-AryA,
   (17) C$_{1-6}$ alkylene-N(R$^A$)C(O)—HetA,
   (18) N(R$^A$)C(O)O—C$_{1-6}$ alkylene-AryA,
   (19) N(R$^A$)C(O)O—C$_{1-6}$ alkylene-HetA,
   (20) O—C$_{1-6}$ alkylene-AryA, or
   (21) O—C$_{1-6}$ alkylene-HetA.

9. The compound according to claim 8, or a pharmaceutically acceptable salt thereof, wherein:
R$^1$ is:
   (1) H,
   (2) C$_{1-4}$ alkyl,
   (3) C$_{1-4}$ alkyl substituted with N(R$^A$)R$^B$ or N(R$^A$)O—C$_{1-4}$ alkyl,
   (4) N(R$^A$)R$^B$,
   (5) N(R$^A$)C(O)—C$_{1-4}$ alkyl,
   (6) N(R$^A$)C(O)—(CH$_2$)$_{1-2}$N(R$^A$)R$^B$,
   (7) N(R$^A$)C(O)—(CH$_2$)$_{1-2}$S(O)$_2$R$^A$,
   (8) N(R$^A$)C(O)C(O)N(R$^A$)R$^B$,
   (9) HetR,
   (10) (CH$_2$)$_{1-2}$-HetR,
   (11) N(R$^A$)C(O)C(O)—HetR,
   (12) N(R$^A$)C(O)-AryA,
   (13) N(R$^A$)C(O)—HetA,
   (14) N(R$^A$)C(O)—HetR,
   (15) N(R$^A$)C(O)—(CH$_2$)$_{1-2}$-AryA,
   (16) N(R$^A$)C(O)—(CH$_2$)$_{1-2}$-HetA,
   (17) N(R$^A$)C(O)—(CH$_2$)$_{1-2}$-HetR,
   (18) (CH$_2$)$_{1-2}$-N(R$^A$)C(O)-AryA,
   (19) (CH$_2$)$_{1-2}$-N(R$^A$)C(O)—HetA,
   (20) N(R$^A$)C(O)O—(CH$_2$)$_{1-2}$-AryA,
   (21) N(R$^A$)C(O)O—(CH$_2$)$_{1-2}$-HetA,
   (22) O—(CH$_2$)$_{1-2}$-AryA, or
   (23) O—(CH$_2$)$_{1-2}$-HetA,
R$^2$, R$^3$, and R$^4$ are each independently H or C$_{1-4}$ alkyl;
R$^5$ is H or C$_{1-4}$ alkyl;
each R$^A$ is independently H or C$_{1-4}$ alkyl;
each R$^B$ is independently H or C$_{1-4}$ alkyl;
AryA is phenyl or naphthyl, wherein the phenyl or naphthyl is optionally substituted with a total of from 1 to 5 substituents, wherein:
   (i) from zero to 5 substituents are each independently:
      (1) C$_{1-4}$ alkyl,
      (2) O—C$_{1-4}$ alkyl,
      (3) C$_{1-4}$ haloalkyl,
      (4) O—C$_{1-4}$ haloalkyl,
      (5) OH,
      (6) halogen,
      (7) CN,
      (8) NO$_2$,
      (9) N(R$^A$)R$^B$,
      (10) C(O)N(R$^A$)R$^B$,
      (11) C(O)—C$_{1-4}$ alkyl,
      (12) CO$_2$—C$_{1-4}$ alkyl,
      (13) S—C$_{1-4}$ alkyl,
      (14) S(O)—C$_{1-4}$ alkyl,
      (15) SO$_2$—C$_{1-4}$ alkyl,
      (16) SO$_2$N(R$^A$)R$^B$,
      (17) SO$_2$N(R$^A$)C(O)—C$_{1-4}$ alkyl, or
      (18) N(R$^A$)C(O)—C$_{1-4}$ alkyl, and
   (ii) from zero to 1 substituent is AryE, HetE, CH$_2$-AryE, or CH$_2$-HetE;
HetA is (i) a 5- or 6-membered heteroaromatic ring containing from 1 to 4 heteroatoms independently selected from N, O and S, wherein each N is optionally in the form of an oxide, or (ii) a 9- or 10-membered bicyclic, fused ring system containing a total of from 1 to 4 heteroatoms independently selected from zero to 4 N atoms, zero to 20 atoms, and zero to 2 S atoms, wherein either one or both of the rings contain one or more of the heteroatoms, at least one ring is aromatic, each N is optionally in the form of an oxide, and each S in a ring which is not aromatic is optionally S(O) or S(O)$_2$; wherein the heteroaromatic ring or the bicyclic, fused ring system is optionally substituted with a total of from 1 to 4 substituents, wherein:
   (i) from zero to 4 substituents are each independently:
      (1) C$_{1-4}$ alkyl,
      (2) O—C$_{1-4}$ alkyl,
      (3) C$_{1-4}$ haloalkyl,
      (4) O—C$_{1-4}$ haloalkyl,
      (5) OH,
      (6) Cl, Br, or F,
      (7) CN,
      (8) C(O)N(R$^A$)R$^B$,
      (9) S(O)$_2$—C$_{1-4}$ alkyl, or
      (10) S(O)$_2$N(R$^A$)R$^B$, and
   (ii) from zero to 1 substituent is AryE, HetE, CH$_2$-AryE, or CH$_2$-HetE;

HetR is a 4- to 7-membered, saturated or mono-unsaturated heterocyclic ring or a 6- to 10-membered saturated or mono-unsaturated, bridged or fused heterobicyclic ring, wherein the heterocyclic or heterobicyclic ring contains a nitrogen atom which is directly attached to the rest of the molecule and optionally contains an additional heteroatom selected from N, O, and S, where the S is optionally oxidized to S(O) or S(O)$_2$; and wherein the heterocyclic or heterobicyclic ring is optionally substituted with a total of from 1 to 4 substituents, wherein:
  (i) from zero to 4 substituents are each independently Cl, Br, F, C$_{1-4}$ alkyl, OH, oxo, C(O)—C$_{1-4}$ alkyl, S(O)$_2$—C$_{1-4}$ alkyl, O—C$_{1-4}$ alkyl, O—C$_{1-4}$ haloalkyl, or C$_{1-4}$ haloalkyl; and
  (ii) from zero to 1 substituent is AryE, HetE, CH$_2$-AryE, or CH$_2$-HetE;

AryB is phenyl which is optionally substituted with from 1 to 5 substituents wherein:
  (i) from zero to 5 substituents are each independently:
    (1) C$_{1-4}$ alkyl,
    (2) OH
    (3) O—C$_{1-4}$ alkyl,
    (4) C$_{1-4}$ haloalkyl,
    (5) O—C$_{1-4}$ haloalkyl,
    (6) halogen,
    (7) CN,
    (8) N(R$^A$)R$^B$,
    (9) C(O)N(R$^A$)R$^B$,
    (10) SR$^A$,
    (11) S(O)R$^A$,
    (12) SO$_2$R$^A$,
    (13) N(R$^A$)SO$_2$R$^B$,
    (14) N(R$^A$)SO$_2$N(R$^A$)R$^B$,
    (15) N(R$^A$)C(O)R$^B$, or
    (16) N(R$^A$)C(O)C(O)N(R$^A$)R$^B$, and
  (ii) from zero to 1 substituent is AryE, HetE, CH$_2$-AryE, or CH$_2$-HetE;

AryE is phenyl which is optionally substituted with from 1 to 3 substituents each of which is independently C$_{1-4}$ alkyl, O—C$_{1-4}$ alkyl, C$_{1-4}$ fluoroalkyl, O—C$_{1-4}$ fluoroalkyl, Cl, Br, F, CN, C(O)N(R$^A$)R$^B$, S(O)$_2$—C$_{1-4}$ alkyl, or S(O)$_2$N(R$^A$)R$^B$; and HetE is a 5- or 6-membered heteroaromatic ring containing from 1 to 4 heteroatoms independently selected from N, O and S, wherein each N is optionally in the form of an oxide, wherein the heteroaromatic ring is optionally substituted with from 1 to 3 substituents each of which is independently Cl, Br, F, CN, NO$_2$, C$_{1-4}$ alkyl, C$_{1-4}$ fluoroalkyl, OH, O—C$_{1-4}$ alkyl, or O—C$_{1-4}$ fluoroalkyl.

10. The compound according to claim 9, or a pharmaceutically acceptable salt thereof, which is a compound of Formula II:

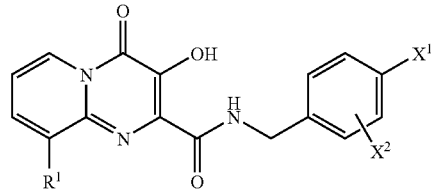

(II)

wherein:
R$^1$ is:
  (1) H,
  (2) C$_{1-4}$ alkyl,
  (3) CH$_2$N(C$_{1-4}$ alkyl)$_2$,
  (4) CH$_2$N(C$_{1-4}$ alkyl)-O—C$_{1-4}$ alkyl,
  (5) N(C$_{1-4}$ alkyl)$_2$,
  (6) N(C$_{1-4}$ alkyl)C(O)—C$_{1-4}$ alkyl,
  (7) N(C$_{1-4}$ alkyl)C(O)CH$_2$N(C$_{1-4}$ alkyl)$_2$,
  (8) N(C$_{1-4}$ alkyl)C(O)CH$_2$S(O)$_2$—C$_{1-4}$ alkyl,
  (9) N(C$_{1-4}$ alkyl)C(O)C(O)(C$_{1-4}$ alkyl)$_2$,
  (10) HetR,
  (11) CH$_2$-HetR,
  (12) N(C$_{1-4}$ alkyl)C(O)C(O)—HetR,
  (13) N(H)C(O)-AryA,
  (14) N(C$_{1-4}$ alkyl)C(O)-AryA,
  (15) N(H)C(O)—HetA,
  (16) N(C$_{1-4}$ alkyl)C(O)—HetA,
  (17) N(H)C(O)—HetR,
  (18) N(C$_{1-4}$ alkyl)C(O)—HetR,
  (19) N(H)C(O)—(CH$_2$)$_{1-2}$-AryA,
  (20) N(C$_{1-4}$ alkyl)C(O)—(CH$_2$)$_{1-2}$-AryA,
  (21) N(H)C(O)—(CH$_2$)$_{1-2}$-HetA,
  (22) N(C$_{1-4}$ alkyl)C(O)—(CH$_2$)$_{1-2}$-HetA,
  (23) N(C$_{1-4}$ alkyl)C(O)CH$_2$-HetR,
  (24) CH$_2$N(H)C(O)-AryA,
  (25) CH$_2$N(C$_{1-4}$ alkyl)C(O)-AryA,
  (26) CH$_2$N(H)C(O)—HetA,
  (27) CH$_2$N(C$_{1-4}$ alkyl)C(O)—HetA,
  (28) N(H)C(O)OCH$_2$-AryA,
  (29) N(C$_{1-4}$ alkyl)C(O)OCH$_2$-AryA,
  (30) N(H)C(O)OCH$_2$-HetA,
  (31) N(C$_{1-4}$ alkyl)C(O)OCH$_2$-HetA,
  (32) OCH$_2$-AryA, or
  (33) OCH$_2$-HetA;

AryA is phenyl which is optionally substituted with from 1 to 3 substituents each of which is independently bromo chloro, fluoro, methoxy, C$_{1-4}$ alkyl, CF$_3$, OCF$_3$, CN, or SO$_2$(C$_{1-4}$ alkyl);

HetA is a heteroaromatic ring selected from the group consisting of pyrrolyl, pyrazolyl, imidazolyl, pyridinyl, pyrimidinyl, pyrazinyl, oxazolyl, isoxazolyl, thiazolyl, isothiazolyl, and oxadiazolyl, wherein the heteroaromatic ring is optionally substituted with from 1 to 2 substituents each of which is independently a C$_{1-4}$ alkyl; and HetR is a heterocyclic ring selected from the group consisting of:

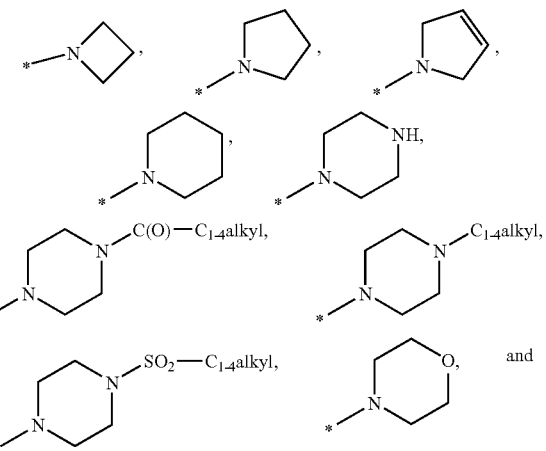

-continued

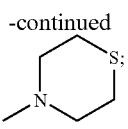

wherein the asterisk denotes the point of attachment of the heterocyclic ring to the rest of the molecule;

$X^1$ is H, bromo, chloro, fluoro, or methoxy; and $X^2$ is H, bromo, chloro, fluoro, methoxy, $C_{1-4}$ alkyl, $CF_3$, $OCF_3$, CN, or $SO_2(C_{1-4}$ alkyl).

11. The compound according to claim 1, or a pharmaceutically acceptable salt thereof, wherein:
$R^3$ is:
(1) halogen,
(2) AryA, or
(3) HetA.

12. The compound according to claim 11, or a pharmaceutically acceptable salt thereof, which is a compound of Formula III:

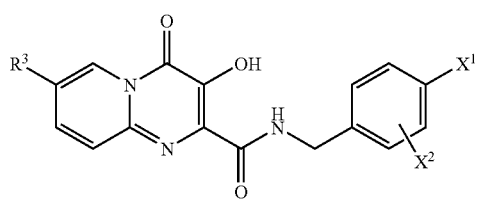

(III)

wherein:
$R^3$ is:
(1) bromine,
(2) AryA, or
(3) HetA;

AryA is phenyl which is optionally substituted with a total of from 1 to 3 substituents, wherein:
(i) from zero to 3 substituents are each independently bromo chloro, fluoro, methoxy, $C_{1-4}$ alkyl, $CF_3$, $OCF_3$, CN, $SO_2(C_{1-4}$ alkyl), or $N(C_{1-4}$ alkyl)$_2$, and
(ii) from zero to 1 substituent is:

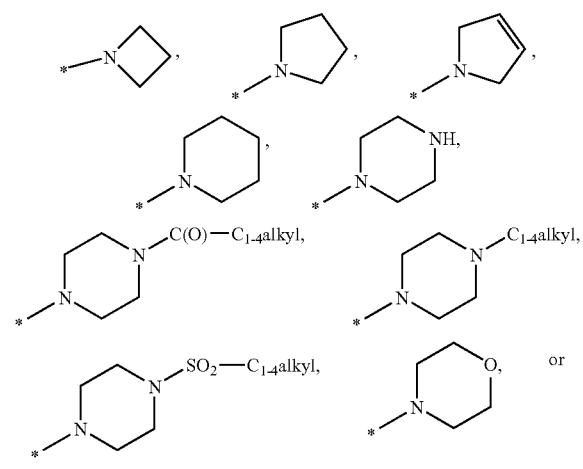

-continued

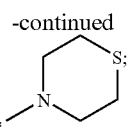

wherein the asterisk denotes the point of attachment of the heterocyclic ring to the rest of the molecule;

HetA is a heteroaromatic ring selected from the group consisting of pyrrolyl, pyrazolyl, imidazolyl, pyridinyl, pyrimidinyl, pyrazinyl, oxazolyl, isoxazolyl, thiazolyl, isothiazolyl, and oxadiazolyl, wherein the heteroaromatic ring is optionally substituted with from 1 to 2 substituents each of which is independently a $C_{1-4}$ alkyl;

$X^1$ is H, bromo, chloro, fluoro, or methoxy; and $X^2$ is H, bromo, chloro, fluoro, methoxy, $C_{1-4}$ alkyl, $CF_3$, $OCF_3$, CN, or $SO_2(C_{1-4}$ alkyl).

13. A compound, or a pharmaceutically acceptable salt thereof, selected from the group consisting of:

N-(4-fluorobenzyl)-3-hydroxy-4-oxo-4H-pyrido[1,2-a]pyrimidine-2-carboxamide;

N-(4-fluorobenzyl)-3-hydroxy-9-{methyl[(methylsulfonyl)acetyl]amino}-4-oxo-4H-pyrido[1,2-a]pyrimidine-2-carboxamide;

N-(4-fluorobenzyl)-3-hydroxy-9-[(N,N,N'-triethyl)-ethanediamide]-4-oxo-4H-pyrido[1,2-a]pyrimidine-2-carboxamide;

N-(4-fluorobenzyl)-3-hydroxy-9-(benzyloxy)-4-oxo-4H-pyrido[1,2-a]pyrimidine-2-carboxamide;

N-(4-fluorobenzyl)-3-hydroxy-7-(2-morpholin-4-ylphenyl)-4-oxo-4H-pyrido[1,2-a]pyrimidine-2-carboxamide;

9-[acetyl(methyl)amino]-N-(4-fluorobenzyl)-3-hydroxy-4-oxo-4H-pyrido[1,2-a]pyrimidine-2-carboxamide;

9-[benzoyl(methyl)amino]-N-(4-fluorobenzyl)-3-hydroxy-4-oxo-4H-pyrido[1,2-a]pyrimidine-2-carboxamide;

9-[methylamino]-N-(4-fluorobenzyl)-3-hydroxy-4-oxo-4H-pyrido[1,2-a]pyrimidine-2-carboxamide;

9-[dimethylamino]-N-(4-fluorobenzyl)-3-hydroxy-4-oxo-4H-pyrido[1,2-a]pyrimidine-2-carboxamide;

9-[ethylamino]-N-(4-fluorobenzyl)-3-hydroxy-4-oxo-4H-pyrido[1,2-a]pyrimidine-2-carboxamide;

N-(2-{[(4-fluorobenzyl)amino]carbonyl}-3-hydroxy-4-oxo-4H-pyrido[1,2-a]pyrimidin-9-yl)-N,N,N-trimethylethanediamide;

N-(2-{[(4-fluorobenzyl)amino]carbonyl}-3-hydroxy-4-oxo-4H-pyrido[1,2-a]pyrimidin-9-yl)-N-ethyl-N',N'-dimethylethanediamide;

benzyl (2-{[(4-fluorobenzyl)amino]carbonyl}-3-hydroxy-4-oxo-4H-pyrido[1,2-a]pyrimidin-9-yl)carbamate;

9-[benzoylamino]-N-(4-fluorobenzyl)-3-hydroxy-4-oxo-4H-pyrido[1,2-a]pyrimidine-2-carboxamide;

9-[ethyl(isonicotinoyl)amino]-N-(4-fluorobenzyl)-3-hydroxy-4-oxo-4H-pyrido[1,2-a]pyrimidine-2-carboxamide;

9-[ethyl(pyridin-2-ylcarbonyl)amino]-N-(4-fluorobenzyl)-3-hydroxy-4-oxo-4H-pyrido[1,2-a]pyrimidine-2-carboxamide;

N-(2-{[(4-fluorobenzyl)amino]carbonyl}-3-hydroxy-4-oxo-4H-pyrido[1,2-a]pyrimidin-9-yl)-N-propyl-N',N'-dimethylethanediamide;

N-(2-{[(4-fluorobenzyl)amino]carbonyl}-3-hydroxy-4-oxo-4H-pyrido[1,2-a]pyrimidin-9-yl)-N-isobutyl-N',N'-dimethylethanediamide;

- N-(4-fluorobenzyl)-3-hydroxy-9-{ethyl[morpholin-4-yl(oxo)acetyl]amino}-4-oxo-4H-pyrido[1,2-a]pyrimidine-2-carboxamide;
- 9-[(N,N-dimethylglycyl)(ethyl)amino]-N-(4-fluorobenzyl)-3-hydroxy-4-oxo-4H-pyrido[1,2-a]pyrimidine-2-carboxamide;
- 9-[(N,N-diethylglycyl)(ethyl)amino]-N-(4-fluorobenzyl)-3-hydroxy-4-oxo-4H-pyrido[1,2-a]pyrimidine-2-carboxamide;
- 9-[ethyl(morpholin-4-ylacetyl)amino]-N-(4-fluorobenzyl)-3-hydroxy-4-oxo-4H-pyrido[1,2-a]pyrimidine-2-carboxamide;
- 9-{ethyl[(4-methylpiperazin-1-yl)acetyl]amino}-N-(4-fluorobenzyl)-3-hydroxy-4-oxo-4H-pyrido[1,2-a]pyrimidine-2-carboxamide;
- 9-[ethyl(1,3-thiazol-4-ylcarbonyl)amino]-N-(4-fluorobenzyl)-3-hydroxy-4-oxo-4H-pyrido[1,2-a]pyrimidine-2-carboxamide;
- 9-[ethyl(isoxazol-5-ylcarbonyl)amino]-N-(4-fluorobenzyl)-3-hydroxy-4-oxo-4H-pyrido[1,2-a]pyrimidine-2-carboxamide;
- 9-{ethyl[(5-methyl-1,3,4-oxadiazol-2-yl)carbonyl]amino}-N-(4-fluorobenzyl)-3-hydroxy-4-oxo-4H-pyrido[1,2-a]pyrimidine-2-carboxamide;
- 9-{ethyl[oxo(pyrrolidin-1-yl)acetyl]amino}-N-(4-fluorobenzyl)-3-hydroxy-4-oxo-4H-pyrido[1,2-a]pyrimidine-2-carboxamide;
- 4-[[ethyl(2-{[(4-fluorobenzyl)amino]carbonyl}-3-hydroxy-4-oxo-4H-pyrido[1,2-a]pyrimidin-9-yl)amino](oxo)acetyl]-1-methylpiperazine;
- N-(4-fluorobenzyl)-3-hydroxy-9-methyl-4-oxo-4H-pyrido[1,2-a]pyrimidine-2-carboxamide;
- 9-[(dimethylamino)methyl]-N-(4-fluorobenzyl)-3-hydroxy-4-oxo-4H-pyrido[1,2-a]pyrimidine-2-carboxamide;
- N-(4-fluorobenzyl)-3-hydroxy-9-{[methoxy(methyl)amino]methyl}-4-oxo-4H-pyrido[1,2-a]pyrimidine-2-carboxamide;
- N-(4-fluorobenzyl)-3-hydroxy-9-(morpholin-4-ylmethyl)-4-oxo-4H-pyrido[1,2-a]pyrimidine-2-carboxamide;
- 9-[(4-acetylpiperazin-1-yl)methyl]-N-(4-fluorobenzyl)-3-hydroxy-4-oxo-4H-pyrido[1,2-a]pyrimidine-2-carboxamide;
- 9-[(benzoylamino)methyl]-N-(4-fluorobenzyl)-3-hydroxy-4-oxo-4H-pyrido[1,2-a]pyrimidine-2-carboxamide; and
- 7-bromo-N-(4-fluorobenzyl)-3-hydroxy-4-oxo-4H-pyrido[1,2-a]pyrimidine-2-carboxamide.

\* \* \* \* \*